US005695933A

United States Patent [19]
Schalling et al.

[11] Patent Number: 5,695,933
[45] Date of Patent: Dec. 9, 1997

[54] DIRECT DETECTION OF EXPANDED NUCLEOTIDE REPEATS IN THE HUMAN GENOME

[75] Inventors: Martin Schalling, Spanga, Sweden; Thomas J. Hudson, Arlington; David E. Housman, Newton, both of Mass.

[73] Assignee: Massachusetts Institute of Technology, Cambridge, Mass.

[21] Appl. No.: 68,747

[22] Filed: May 28, 1993

[51] Int. Cl.$^6$ .............................. C12Q 1/68; C12P 19/34
[52] U.S. Cl. ......................... 435/6; 435/91.2; 435/91.52
[58] Field of Search .................. 435/91.52, 6; 436/177, 436/514; 935/77

[56] References Cited

U.S. PATENT DOCUMENTS

5,075,217  12/1991  Weber .......................................... 435/6

FOREIGN PATENT DOCUMENTS

| 0246864 | 11/1987 | European Pat. Off. . |
| 0439182 | 7/1991 | European Pat. Off. . |
| 0 552 545 A1 | 7/1993 | European Pat. Off. . |
| 93/16196 | 8/1993 | WIPO . |
| 93/16197 | 8/1993 | WIPO . |

OTHER PUBLICATIONS

Smith et al, Life Science Abstract, Nucleic Acid Res., 21(3), 1993, pp. 755–756.
Schalling, M. et al., "Direct Deteection of Novel Expanded Trinucleotide Repeats in the Human Genome," *Nature Genetics*, 4:135–139 (1993).
Schumm, J.W., et al., "Identification of More than 500 RFLPs by Screening Random Genomic Clones", Am. J. Hum. Genet. 42:143–159 (1988).
Biancalana, et al., "Moderate instability of the trinucleotide repeat in spino bulbar muscular atrophy", Human Molecular Genetics, 1(4):255–258 (1992).
Beckmann, J.S. and Weber, J.L., "Survey of Human and Rat Microsatellites" Genomics, 12:627–631 (1992).
Riggins, G.J., et al., "Human genes containing polymorphic trinucleotide repeats", Nature Genetics 2:186–191 (1992).
Verkerk, A.J.M.H., et al., "Identification of a Gene (FMR-1) Containing a CGG Repeat Coincident with a Breakpoint Cluster Region Exhibiting Length Variation in Fragile X Syndrome", Cell, 65:905–914 (1991).

Brook, J. D., et al., "Molecular Basis of Myotonic Dystrophy: Expansion of a Trinucleotide (CTG) Repeat at the 3' End of a Transcript Encoding a Protein Kinase Family Member", Cell, 68:799–808 (1992).
Gusella, J.F., et al., "A Novel Gene Containing a Trinucleotide Repeat That is Expanded and Unstable on Huntington's Disease Chromosomes" Cell, 72:971–983 (1993).
La Spada, A.R., et al., "Androgen receptor gene mutations in X–linked spinal and bulbar muscular atrophy", Nature, 352:77–79 (1991).
Goodfellow P.N., "Planting Alfalfa and Cloning the Huntington's Disease Gene", Cell, 72:817–818, (1993).
Aslanidis, C., et al., "Cloning of the essential myotonic dystrophy region and mapping of the putative defect", Nature, 355:548–551 (1992).
Buxton, J., et al., "Detection of an unstable fragment of DNA specific to individuals with myotonic dystrophy", Nature, 355:547–548 (1992).
Goldberg, Y.P., et al., "Identification of an Alu retrotransposition event in close proximity to a strong candidate gene for Huntington's disease" Nature, 362:370–373 (1993).
Richards R.I., and Sutherland, G.R., "Heritable unstable DNA sequences" Nature Genetics, 1:7–9 (1992).
Webb, T.P., et al., "Population Incidence and Segregation Ratios in the Martin–Bell Syndrome", American Journal of Medical Genetics 23:573–580 (1986).
Skolnick, M.H., and Wallace, R.B., "Simultaneous Analysis of Multiple Polymorphic Loci Using Amplified Sequence Polymorphisms (ASPs)", Genomics 2:273–279 (1988).
Gustavson, K.–H., et al., "Prevalence of the Fragile–X Syndrome in Mentally retarded boys in a Swedish County", American Journal of Medical Genetics 23:581–587 (1986).
Harley, H.G., et al., "Expansion of an unstable DNA region and phenotypic variation in myotonic dystrophy", Nature 355:545–546 (1992).

*Primary Examiner*—David Guzo
*Attorney, Agent, or Firm*—Hamilton, Brook, Smith & Reynolds, P.C.

[57] ABSTRACT

Methods of detecting expanded nucleotide repeats in genomic DNA in a biological sample are disclosed and methods for the diagnosis of pathological and potentially pathological conditions in an individual based on the detection of the presence of expanded nucleotide repeats.

45 Claims, 8 Drawing Sheets

SEQUENCE LISTING ( 1 ) GENERAL INFORMATION:

( i i i ) NUMBER OF SEQUENCES: 11

( 2 ) INFORMATION FOR SEQ ID NO:1:

( i ) SEQUENCE CHARACTERISTICS:
        ( A ) LENGTH: 51 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="synthetic"

( x i ) SEQUENCE DESCRIPTION: SEQ ID NO:1:

```
CTGCTGCTGC TGCTGCTGCT GCTGCTGCTG CTGCTGCTGC TGCTGCTGCT G        51
```

( 2 ) INFORMATION FOR SEQ ID NO:2:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="Synthetic"

( x i ) SEQUENCE DESCRIPTION: SEQ ID NO:2:

```
CCGCCGCCGC CGCCGCCGCC GCCGCCGCCG        30
```

( 2 ) INFORMATION FOR SEQ ID NO:3:

( i ) SEQUENCE CHARACTERISTICS:

( A ) LENGTH: 30 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="Synthetic"

( x i ) SEQUENCE DESCRIPTION: SEQ ID NO:3:

CCACCACCAC CACCACCACC ACCACCACCA                    30

( 2 ) INFORMATION FOR SEQ ID NO:4:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="Synthetic"

( x i ) SEQUENCE DESCRIPTION: SEQ ID NO:4:

AGGAGGAGGA GGAGGAGGAG GAGGAGGAGG                    30

( 2 ) INFORMATION FOR SEQ ID NO:5:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="Synthetic"

( x i ) SEQUENCE DESCRIPTION: SEQ ID NO:5:

ACGACGACGA CGACGACGAC GACGACGACG                    30

( 2 ) INFORMATION FOR SEQ ID NO:6:

( i ) SEQUENCE CHARACTERISTICS:
        ( A ) LENGTH: 30 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="Synthetic"

( x i ) SEQUENCE DESCRIPTION: SEQ ID NO:6:

CAGCAGCAGC AGCAGCAGCA GCAGCAGCAG                    30

( 2 ) INFORMATION FOR SEQ ID NO:7:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: other nucleic acid
        ( A ) DESCRIPTION: /desc ="Synthetic"

( x i ) SEQUENCE DESCRIPTION: SEQ ID NO:7:

CGGCGGCGGC GGCGGCGGCG GCGGCGGCGG CGG                 33

( 2 ) INFORMATION FOR SEQ ID NO:8:

( i ) SEQUENCE CHARACTERISTICS:

(A) LENGTH: 36 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc ="Synthetic"

(xi) SEQUENCE DESCRIPTION: SEQ ID NO:8:

TGGTGGTGGT GGTGGTGGTG GTGGTGGTGG TGGTGG    36

(2) INFORMATION FOR SEQ ID NO:9:

(i) SEQUENCE CHARACTERISTICS:
        (A) LENGTH: 39 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc ="Synthetic"

(xi) SEQUENCE DESCRIPTION: SEQ ID NO:9:

CCTCCTCCTC CTCCTCCTCC TCCTCCTCCT CCTCCTCCT    39

(2) INFORMATION FOR SEQ ID NO:10:

(i) SEQUENCE CHARACTERISTICS:
        (A) LENGTH: 42 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc ="Synthetic"

(xi) SEQUENCE DESCRIPTION: SEQ ID NO:10:

CGTCGTCGTC GTCGTCGTCG TCGTCGTCGT CGTCGTCGTC GT    42

(2) INFORMATION FOR SEQ ID NO:11:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc ="Synthetic"

(xi) SEQUENCE DESCRIPTION: SEQ ID NO:11:

CTGCTGCTGC TGCTGCTGCT GCTGCTGCTG    30

DIRECT DETECTION OF EXPANDED NUCLEOTIDE REPEATS IN THE HUMAN GENOME

GOVERNMENT SUPPORT

Work described herein was supported by the Center for Genome Research Grants HG 00299 and P50-HG 00098, the Swedish Medical Research Council, Svenska Lakaresallskapet and Wenner Gren Foundation.

INTRODUCTION

The presence of unstable DNA sequences, such as the expansion of simple nucleotide sequence repeats in genomic DNA, has recently been implicated as a mechanism leading to genetic disorders or conditions. Expansion of trinucleotide repeat sequences occurs in fragile X syndrome (FX), the most common form of familial mental retardation (Webb, T. P., et al., *Am. J. Med. Genet.*, 23:573–580 (1986); Gustavson, K. H., et al., *Am. J. Med. Genet.*, 23:581–588 (1986)), myotonic dystrophy (MD), an autosomal dominant disease which is a leading cause of inherited muscle weakness, (Harper, P. S., MYOTONIC DYSTROPHY, 2d Ed., London, England, W. B. Saunders Co. (1989), spino bulbal muscular atrophy (SBMA, or Kennedy disease) (LaSpada, A. R., et al., *Nature*, 352:77–79 (1992)), and Huntington's disease, a progressive neurodegenerative disorder (MacDonald, M. E., et al., *Cell*, 72:971–983 (1993)).

The identification of these conditions in which repeat expansions play a key role in clinical etiology raises the prospect that additional pathological conditions may be the consequence of repeat expansions. However, the technical challenges in identifying such additional conditions are significant. For MD, FX, SBMA and HD, several methods have been used to identify repeat expansions once the gene which is associated with the condition was located by positional cloning. PCR-based diagnostic assays have also been useful, but only if unique DNA sequences flanking the repeat have been previously determined. (Brook, J. D., et al., *Cell*, 68:905–914 (1992)). Moreover, PCR has been ineffective when the repeat size reaches several hundred nucleotides or more.

Southern blotting can be used to detect alleles containing expanded repeats greater than a few hundred nucleotides, but also requires that a probe flanking the repeat be available. Thus, new strategies are needed to directly identify repeat expansions of clinical significance in a simple and fast procedure.

Furthermore, the occurrence of expanded nucleotide repeats in these conditions raises the question of how general this phenomenon may be in the etiology of genetic conditions. A general strategy for the direct detection of nucleotide repeat expansion in the human genome would provide a direct approach to address this significant issue in medical genetics.

SUMMARY OF THE INVENTION

The present invention relates to a method of detecting expanded nucleotide repeats in genomic DNA in a biological sample. Specifically, this method relates to detecting an expanded trinucleotide repeat in genomic DNA.

The present invention further relates to methods of diagnosis of pathological and potentially pathological conditions (i.e., genetic conditions) in an individual, based on the detection of the presence of an expanded nucleotide repeat.

The present method is carried out as follows. Genomic DNA contained in a biological sample is rendered available for annealing (hybridizing) with complementary oligonucleotides. In particular, genomic DNA is isolated and combined with simple sequence repeat oligonucleotides (e.g., di-, tri-, or tetranucleotides) having a nucleotide sequence (i.e., nucleic acid sequence) complementary to a nucleotide repeat to be detected in the genomic DNA. The resulting combination of genomic DNA and simple sequence repeat nucleotides is maintained under conditions sufficient for the simple sequence repeat oligonucleotides to anneal to the isolated genomic DNA. If the genomic DNA includes the nucleotide repeat to be detected (i.e., a sequence complementary to the simple sequence repeat oligonucleotide), annealing of the two complementary sequences occurs, resulting in the formation of genomic DNA/annealed simple sequence repeat oligonucleotide complexes. That is, if the repeat sequence to be detected is present in the genomic DNA, the simple sequence repeat oligonucleotides anneal to the genomic DNA, which serves as a support, or template, for annealing.

The genomic DNA/annealed oligonucleotide complexes produced by the annealing step are then maintained under conditions sufficient for ligation of annealed oligonucleotides. If an expanded nucleotide repeat is present in the genomic DNA, the simple sequence repeat oligonucleotides, annealed in close proximity to each other on the genomic DNA support, are ligated and produce multimers of the annealed oligonucleotides. Ligation occurs through the action of an appropriate thermostable ligating enzyme. The ligation step produces multimers of the annealed simple sequence repeat oligonucleotides annealed to regions of the genomic DNA which include the nucleotide repeat to be detected (i.e., the genomic DNA/annealed oligonucleotide complex). The resulting products are referred to herein as genomic DNA/annealed multimer complexes.

The genomic DNA/annealed multimer complex produced by the ligating step is maintained under conditions sufficient for denaturation of the genomic DNA/annealed multimer complexes, resulting in release of the annealed multimers from the genomic DNA/annealed multimer complex and produces unannealed multimers. These steps of annealing, ligating and denaturing are repeated until sufficient copies of unannealed multimers are available for detection. The presence of unannealed multimers is an indication of the presence of an expanded nucleotide repeat in the genomic DNA. That is, the multimers are characteristic of a genetic condition to be diagnosed.

In one embodiment, the presence of unannealed multimers is determined, or detected, by separating, on the basis of size, unannealed multimers, such as by polyacrylamide gel electrophoresis (PAGE). The gel is then electrotransferred to, or blotted onto, a membrane, or filter paper, suitable for use in a hybridization step, thus transferring the unannealed multimers to be detected onto the membrane.

For hybridization, labeled oligonucleotides having nucleic acid sequences complementary to the unannealed multimers to be detected are used as hybridization probes to determine the presence of unannealed multimers blotted onto (present on) the membrane. After hybridization, the pattern of labeled oligonucleotide probes hybridized to the unannealed multimers present on the membrane is visualized. The resulting pattern is an indication of the presence of multimers of specific size. For example, if an expanded CTG nucleotide repeat is present in the genomic DNA, and the $(CTG)_{17}$ (SEQ ID NO:1) simple sequence repeat oligonucleotide is the repeat oligonucleotide used in the method, unannealed multimers will be present in multiples of 17 (i.e., 17, 34, 51, 102, 119 and so forth). The size (i.e., length) of the multimer is an indication of the length of the expanded nucleotide repeat present in the genomic DNA. In the case of a specific genetic condition, the length of the multimer is characteristic of that condition. For example, in the case of MD, the presence of a CTG-repeat containing multimer of more than 100 CTG repeats is characteristic of MD.

In one embodiment, the labeled oligonucleotide probes used for hybridization are $(CCG)_{10}$; $(CCA)_{10}$; $(AGG)_{10}$; $(ACG)_{10}$ and $(CAG)_{10}$ (SEQ ID NOS:2-6 respectively). One type of labeled oligonucleotide probe (i.e., all probes used have the same nucleic acid sequence) is used if one type of simple sequence repeat oligonucleotide was used in the annealing step. Alternately, if a mixture of simple sequence repeat oligonucleotides was used in the annealing step, (e.g., four different types of repeat oligonucleotides, each type having a different simple nucleotide sequence repeat) a mixture of labeled oligonucleotide probes is used in the hybridization step.

The labeled oligonucleotide probes used for hybridization can be labeled with a radioactive label, such as $^{32}P$. In this case, the detectable multimers are visualized by autoradiography. Alternately, the labeled oligonucleotides can be labeled with non-radioactive labels such as peroxidase, biotin or digoxigenin, and the multimers visualized by color developed by enzyme activity or chemiluminescence.

In one embodiment, the present method detects an expanded trinucleotide repeat and the simple sequence repeat oligonucleotides are trinucleotide repeats. Such repeats have, for example, the following sequences: $(CGG)_{11}$; $(TGG)_{12}$; $(CCT)_{13}$; $(CGT)_{14}$ (SEQ ID NOS:7-10 respectively) and $(CTG)_{17}$ (SEQ ID NO:1). One type of oligonucleotide (i.e., oligonucleotides which all have the same nucleic acid sequence) can be used in the annealing step, or more than one type (i.e., a mixture of different types) of oligonucleotides can be used.

In another embodiment of the present method, specific locations of the genomic DNA can be assayed to detect the presence of an expanded nucleotide repeat. In this embodiment, the simple sequence repeat oligonucleotides complementary to the expanded nucleotide repeat to be detected in the genomic DNA are mixed with primer sequences (which are not simple sequence repeat oligonucleotides) that are complementary to known flanking sequences of a given locus on the genomic DNA. Thus, the annealing/ligation mixture includes the simple sequence repeat oligonucleotides, which anneal to nucleotide repeats present in the genomic DNA, and additionally, primer, or flanking, sequences, which anneal to a flanking sequence at a specific locus of the genomic DNA. Ligation of this locus-specific sequence to the simple sequence repeat oligonucleotides generates hybrid molecules containing multimers of the repeat oligonucleotides plus the locus-specific sequence. These hybrid molecules are referred to as locus-specific multimers. Detection of locus-specific multimers is an indication of an expanded nucleotide repeat at a specific location of the genomic DNA.

The present invention also relates to methods of direct identification of pathological and potentially pathological repeat expansions in an individual. Expanded nucleotide repeats have been shown to be present in a number of genetic conditions, especially those associated with anticipation (i.e., with a genetic condition in which the responsible gene is passed on from parent to child, and there is a tendency to earlier onset and increased severity of the condition with succeeding generations). Studies have recently demonstrated that for conditions such as FX, MD, SBMA and HD, a correlation between nucleotide repeat size (i.e., length, or number of repeats) and age of onset of condition symptoms and severity of the condition. Thus, the methods described herein provide a technique for the detection of clinically significant repeat expansions, which are characteristic for a specific genetic condition.

The methods of the present invention, hereinafter referred to as "Repeat Expansion Detection" or RED, are novel, generally applicable methods by which expanded (i.e., elongated or extended) nucleotide repeats are detected without prior knowledge of chromosomal location. The term expanded, as used herein, describes the amplification of, or increased number of repeats of, a simple nucleotide repeat sequence which is present in genomic DNA. For example, a CGG trinucleotide repeat in the 5' untranslated region of the FMR-1 gene transcript is normally polymorphic, having from 6–54 repeats, with a mean of 29 copies. (Riggins, G. J., et al., Nature Genetics, 2:186–191 (1992)). This repeat is unstable in fragile X families, with repeat lengths expanding in length from 52–200 repeats in affected individuals, and, in some cases, expanding up to approximately 1000 copies. (Riggins, G. J., et al., Nature Genetics, 2:186–191 (1992)).

RED is both a sensitive tool in the identification of known nucleotide repeats, such as in fragile X and myotonic dystrophy patients, as well as a tool in the identification and study of novel repeats. RED is also useful as a screening procedure to screen a large population of samples to identify nucleotide repeats characteristic of a genetic condition. RED is based on the use of genomic DNA to support the annealing and ligation of repeat-specific oligonucleotides. Consequently, it does not require flanking sequence information, or single copy probes, as in PCR-based methods. Moreover, RED can be used to detect several repeats with differing core sequences by the inclusion of different types of simple sequence repeat oligonucleotides in the same reaction. As shown by the data presented herein, RED is a fast and simple method that can be applied to the detection of any type of simple nucleotide sequence repeat expansion in the genome. Thus, this method constitutes a unique way of studying other inherited disorders, particularly those characterized by anticipation.

DETAILED DESCRIPTION OF THE INVENTION

Figure 1:
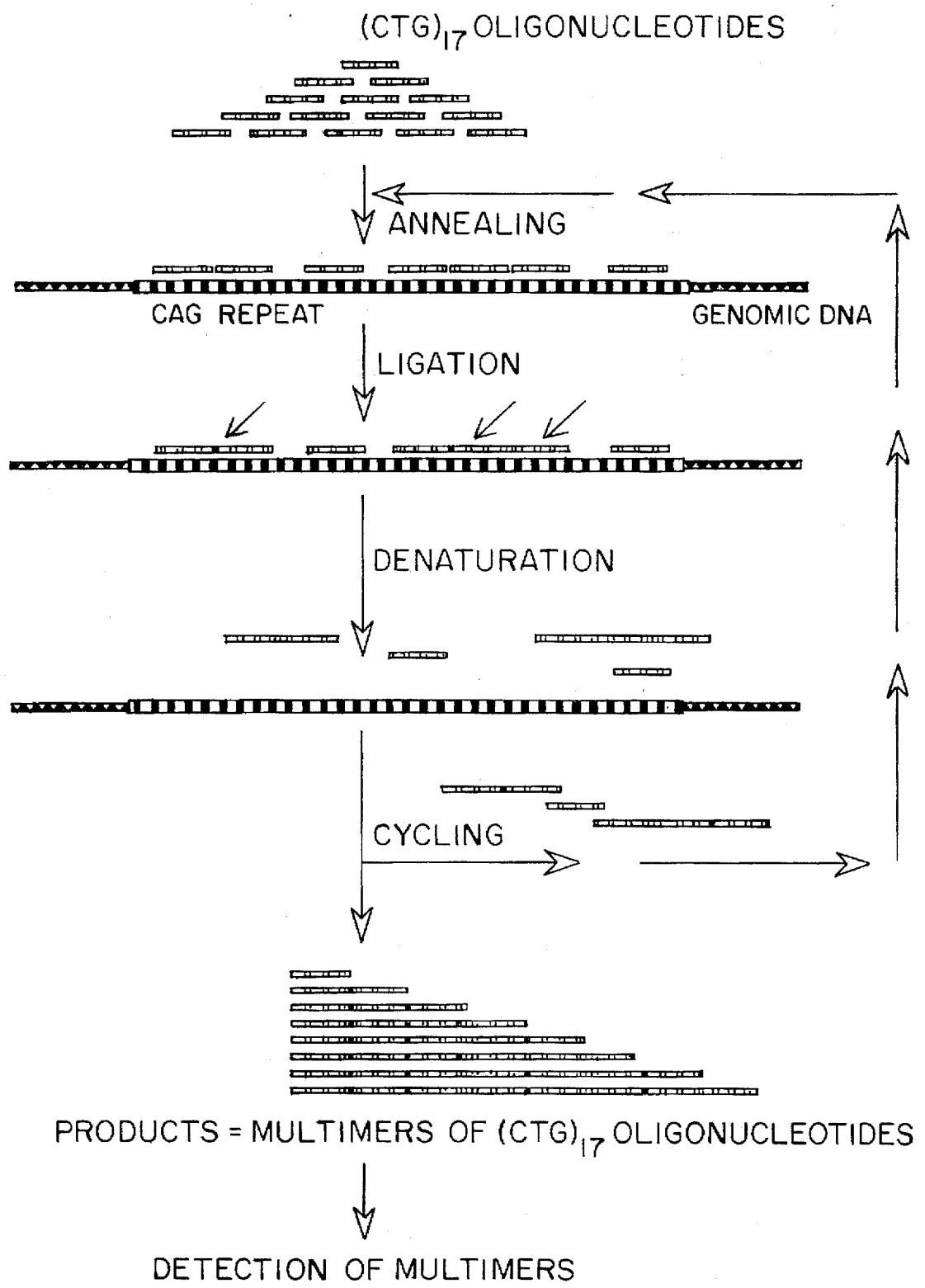
FIG. 1 is a diagram outlining the steps of RED using $(CTG)_{17}$ (SEQ ID NO:1) oligonucleotides.

The present invention relates to a novel, generally applicable method, or technique, termed "Repeat Expansion Detection" hereinafter RED, by which pathological and potentially pathological repeat nucleotide expansion is identified in genomic DNA without prior knowledge of the chromosomal location of the repeat. A diagram outlining the steps of RED is shown in FIG. 1. The RED method described herein in detail and performed as described in Example 1, is as follows.

Production of Multimers

Genomic DNA contained in a biological sample, such as tissue, plasmids, cells or blood, is rendered available for annealing (hybridization) with oligonucleotides and subsequent ligation. Genomic DNA is isolated using commercially available products (e.g., Qiagen Genomic DNA Kit), or standard laboratory techniques, such as those described in Sambrook, J., et al., MOLECULAR CLONING: A LABORATORY MANUAL, 3d Ed., Cold Spring Harbor Laboratory Press (1989).

The isolated genomic DNA is combined as described in detail in Example 1, with simple sequence repeat oligonucleotides (e.g., di-, tri-, or tetranucleotides) having a nucleotide sequence complementary to the nucleotide repeat to be detected in the genomic DNA. As described in Example 1, the simple sequence repeat oligonucleotide was the trinucleotide, CTG. However, other simple sequence repeat oligonucleotides can be used in RED, such as CGG, TGG, CCT, and CGT.

In Example 1, a simple sequence repeat oligonucleotide having 17 repeats of the simple sequence repeat, $(CTG)_{17}$, (SEQ ID NO:1) was used. However, the size of the oligonucleotide can vary from fewer than 11 repeats of the repeat to greater than 17 repeats. For example, although a 17-mer (i.e., containing 17 copies) of the trinucleotide CTG, $(CTG)_{17}$ was used in Example 1, the RED assay has also been performed using a range of lengths of the CTG trinucleotide, with as few as 7 CTG repeats in an oligonucleotide, or as many as 17. Good results were obtained with the length varying from between 8–17 repeats. However, longer simple sequence repeat oligonucleotides can also be effectively used.

The resulting combination of genomic DNA and simple sequence repeat oligonucleotides is maintained under conditions sufficient for the simple sequence repeat oligonucleotides to anneal to the isolated genomic DNA. If the genomic DNA includes the nucleotide repeat to be detected (i.e., complementary to the simple sequence repeat oligonucleotide), annealing of the two complementary sequences occurs, resulting in the formation of complexes (i.e., genomic DNA/annealed simple sequence repeat oligonucleotide complexes, or genomic DNA/annealed oligonucleotide complexes). That is, the genomic DNA serves as a template, or support, which, if the repeat sequence to be detected is present in the genomic DNA, allows for the annealing, or hybridization, of simple sequence repeat oligonucleotides to the genomic DNA.

The temperature used for the annealing reaction can vary depending on the simple sequence repeat oligonucleotide used and the expanded repeat nucleotide to be detected. Generally, the annealing step takes place at a temperature at, or near, the melting point of the genomic DNA. Typically, the annealing step is performed at temperatures ranging from 50°–90° C., most typically at temperatures occurring at between 50°–85° C. For example, using the $(CTG)_{17}$ (SEQ ID NO:1) simple sequence repeat oligonucleotide, as described in Example 1, the annealing temperature was 80° C.

The genomic DNA/annealed oligonucleotide complexes produced by the annealing step are then maintained under conditions sufficient for ligation to occur. If an expanded nucleotide repeat is present in the genomic DNA, the simple sequence repeat oligonucleotides annealed in close proximity to each other on the genomic DNA support are ligated and produce multimers of the annealed oligonucleotides. A thermostable ligase is used (Baranay, F., Proc. Natl. Acad. Sci. USA, 88:189–193 (1991)), which covalently binds only adjacent oligonucleotides (i.e., those in close proximity to each other). Thus, genomic DNA/annealed multimer complexes are formed.

The ligating step can be carried out over a wide range of temperatures, depending on the activity of the enzyme used. Generally, a range of 37°–90° C. can be used, and typically, the temperature is used the same as the temperature used for the annealing step. For example, as described in Example 1, the ligating step which ligated the $(CTG)_{17}$ (SEQ ID NO:1) repeat oligonucleotides into multimers was also performed at 80° C., the same temperature as the annealing step.

The concentration of the ligating enzyme can be varied according to the activity of the enzyme used. As described in Example 1, 5 Units of Ampligase was used. However, good results were obtained with concentrations as low as approximately 1.0 U and as high as approximately 25 U. Results suggest that increasing the concentration of ligating enzyme will also increase the efficiency of the ligation reaction (e.g., an increased yield of the number of multimers produced in less time).

The genomic DNA/annealed multimer complexes produced by the ligating step are then maintained under conditions sufficient for denaturation of the multimer complex, which releases the annealed multimers from the genomic DNA/annealed multimer complex and produces unannealed multimers. Denaturation is typically accomplished by heating the genomic DNA/annealed multimer complex to a temperature sufficient for the release of the multimers from the genomic DNA support. The temperature range used for the denaturation step may vary according to the genomic DNA and simple sequence repeat oligonucleotide used. Standard laboratory conditions for heat denaturation of DNA are used. Typically, the denaturation temperature is approximately 94° C.

One "cycle" of the present method consists of annealing, ligating and denaturing. The method is repeated (enough cycles are allowed to occur) until a sufficient number of unannealed multimers of a desired length are obtained for detection. A desired length is that which demonstrates the presence of an expanded nucleotide repeat of interest, such as an expanded nucleotide repeat known or suspected to be characteristic of a genetic condition. Typically, several hundred cycles are repeated to obtain a sufficient number of multimers. As described herein, a sufficient number of multimers for detection have been produced with as few as 25 cycles. Typically, 25–400 cycles are used and 100–400 have been shown to be particularly effective. As many as 1000 cycles has not resulted in degradation of the detectable product. Thus, a range of 25–1000 cycles will produce a sufficient number multimers for detection (i.e., detectable multimers).

The cycling steps are particularly adaptable to be performed in commercially available thermocyclers, such as the Perkin Elmer/Cetus PCR System 9600; MJ Research Thermocycler PTC 100-96V or the EriComp Thermocycler. Preferably, an oil-free thermocycler with a heated lid is used.

Detection of Multimers

Figure 2:
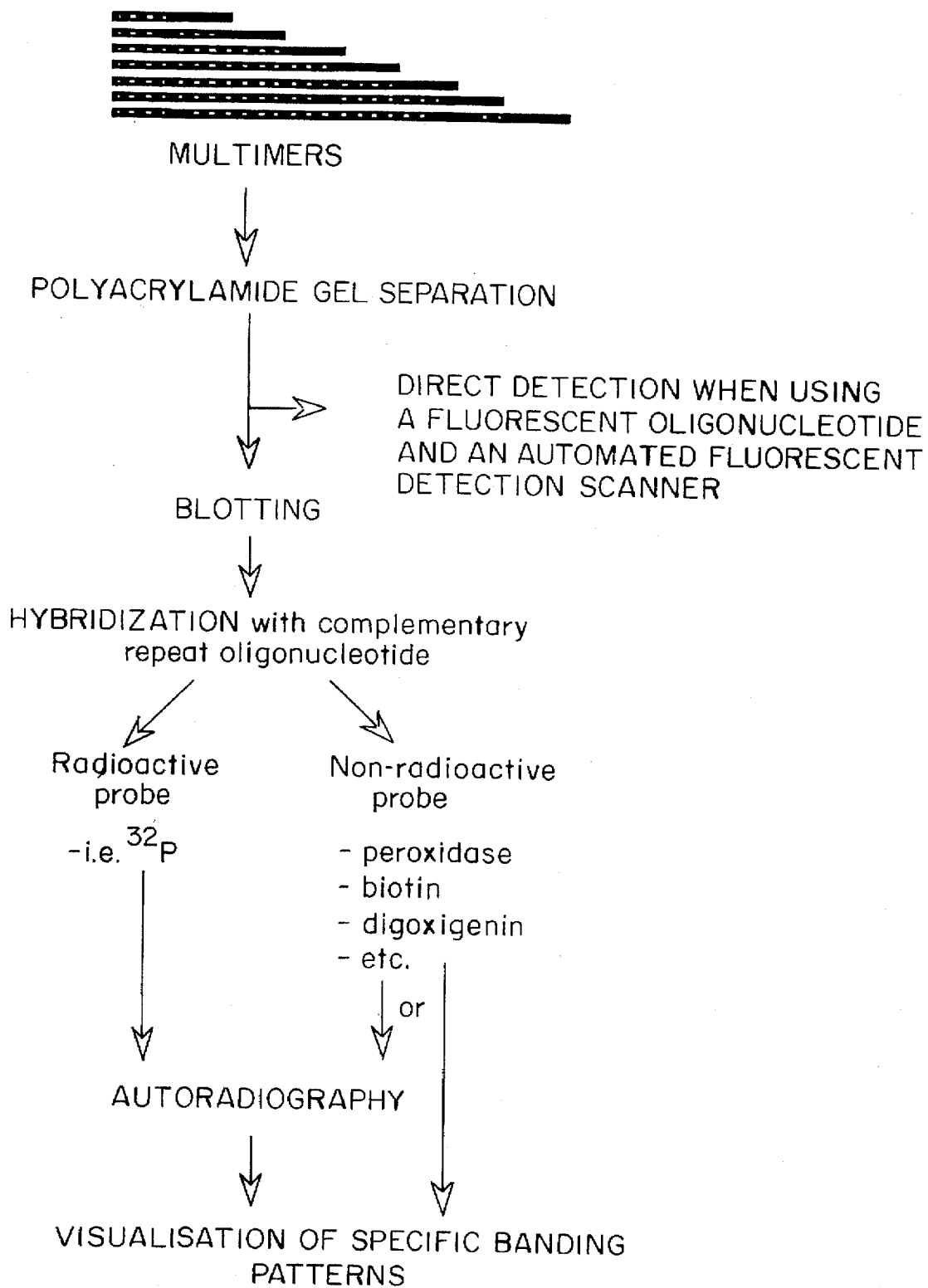
FIG. 2 is a diagram outlining the steps of the detection of RED multimers.

The unannealed multimers produced vary in length as multimers of the oligonucleotides used depending upon the length of the repeat(s) present in the genomic DNA being assayed. These unannealed multimers can be detected by several methods, such as those shown in FIG. 2. In one embodiment, the method includes a size separation step, such as by polyacrylamide gel electrophoresis (PAGE) on a denaturing gel, to distinguish the shorter and more common ligation products from the longer expanded multimers. In the method described in Example 1, the gel was electrotransferred (blotted) to filter paper, which was suitable for use in a hybridization reaction, thus, transferring the unannealed multimers to the filter paper. The filter paper, with the unannealed multimers present, was then hybridized with labeled oligonucleotide probes having sequences complementary to the multimers to be detected. For example, probes selected from the following: $(CCG)_{10}$, $(CCA)_{10}$, $(AGG)_{10}$, $(ACG)_{10}$ and $(CAG)_{10}$ (SEQ ID NO:2–6 respectively) can be used. To maximize product detection, the labeled probe of Example 1 was labeled with multiple $^{32}P$ (dATP molecules at the 3' ends). The hybridization products (i.e., unannealed multimers hybridized with the labeled oligonucleotide probes) were then visualized by autoradiography, performed according to standard laboratory techniques. A pattern of hybridization products (e.g., a pattern of unannealed multimers varying in size from a few repeats to several hundred repeats, such as in ladder configuration) can be visualized. Alternatively, hybridization products of specific lengths which are characteristic of a genetic condition can be visualized. In either case, the visualization of the hybridization products is an indication of the presence of unannealed multimers.

Alternately, the probes can be labeled by non-radioactive molecules, such as peroxidase, biotin and digoxigenin. Visualization of detectable multimers using these non-radioactive probes can be accomplished by color development by enzyme assay, binding to labeled strepavidin, or chemiluminescence.

In another embodiment of RED, fluorescent-tagged simple sequence repeat oligonucleotides in the annealing/ligation/denaturing cycles are used. Multimer products can then be detected by a fluorescent detection scanner after size separation. This embodiment is particularly useful for adaptation for automated detection of multimers.

In a preferred embodiment, RED detects expanded, or elongated, trinucleotide repeats. However, RED is useful in analyzing expanded repeats other than trinucleotides. Dinucleotide, as well as tetranucleotide repeats are abundant in the genome (Beckman, J. S., et al., *Genomics*, 12:627–631 (1992)). RED can also be used to detect long expansions of these repeats as well. Expanded di-, tetra-, penta-, or even longer simple sequence repeats located in genes could also cause dysfunction of genes, possibly leading to pathological conditions. Di-, tetra-, penta- or longer nucleotide repeats can be detected with RED. In any case, whether di-, tri-, tetra- or other expanded repeat nucleotides are to be detected using RED, the appropriate simple sequence repeat oligonucleotide to be used is one that is complementary to one of the strands of the expanded nucleotide repeat to be detected in the genomic DNA.

In one embodiment, the simple sequence repeat oligonucleotides used in RED have one of the following sequences: $(CGG)_{11}$, $(TGG)_{12}$, $(CCT)_{13}$, $(CGT)_{14}$ and $(CTG)_{17}$. However, other simple sequence repeats can also be used in RED, such as AAC, AAG or ACT. All possible combinations of di-, tri-, tetra-, or other simple sequence repeat nucleotides, which are complementary to one of the strands of the expanded nucleotide repeat to be detected in the genomic DNA, can be used in RED.

In another embodiment of the present invention, a mixture of different types of simple sequence repeat oligonucleotides has been used. As described in detail in Example 3, a mixture of four simple sequence repeat oligonucleotides chosen from the following, $(CGG)_{11}$, $(TGG)_{12}$, $(CCT)_{13}$, $(CGT)_{14}$ (SEQ ID NO:7–10 respectively) or $(CTG)_{17}$ (SEQ ID NO:1) was used. This embodiment of RED, called "multiplex RED", permits a single sample of genomic DNA to be tested for the presence of a number of different types of expanded repeats at one time.

Additionally, varying the length of the simple sequence repeat oligonucleotide can increase the resolution of nucleotide repeat expansions. For example, in a genetic condition such as myotonic dystrophy, it is important to distinguish between multimers containing 10 CTG repeats (e.g., in an unaffected individual) and multimers containing 90 CTG repeats (e.g., an affected individual). In this case, a simple sequence repeat oligonucleotide such as a $(CTG)_{10}$ (SEQ ID NO:11) can be used rather than a $(CTG)_{17}$ (SEQ ID NO:1) oligonucleotide. Thus, multimers in multiples of 10 can be detected, (e.g., 10, 30, 90, or 100), rather than multimers in multiples of 17 (e.g., 17, 34, 51, or 102).

Locus-Specific RED

Figure 3:
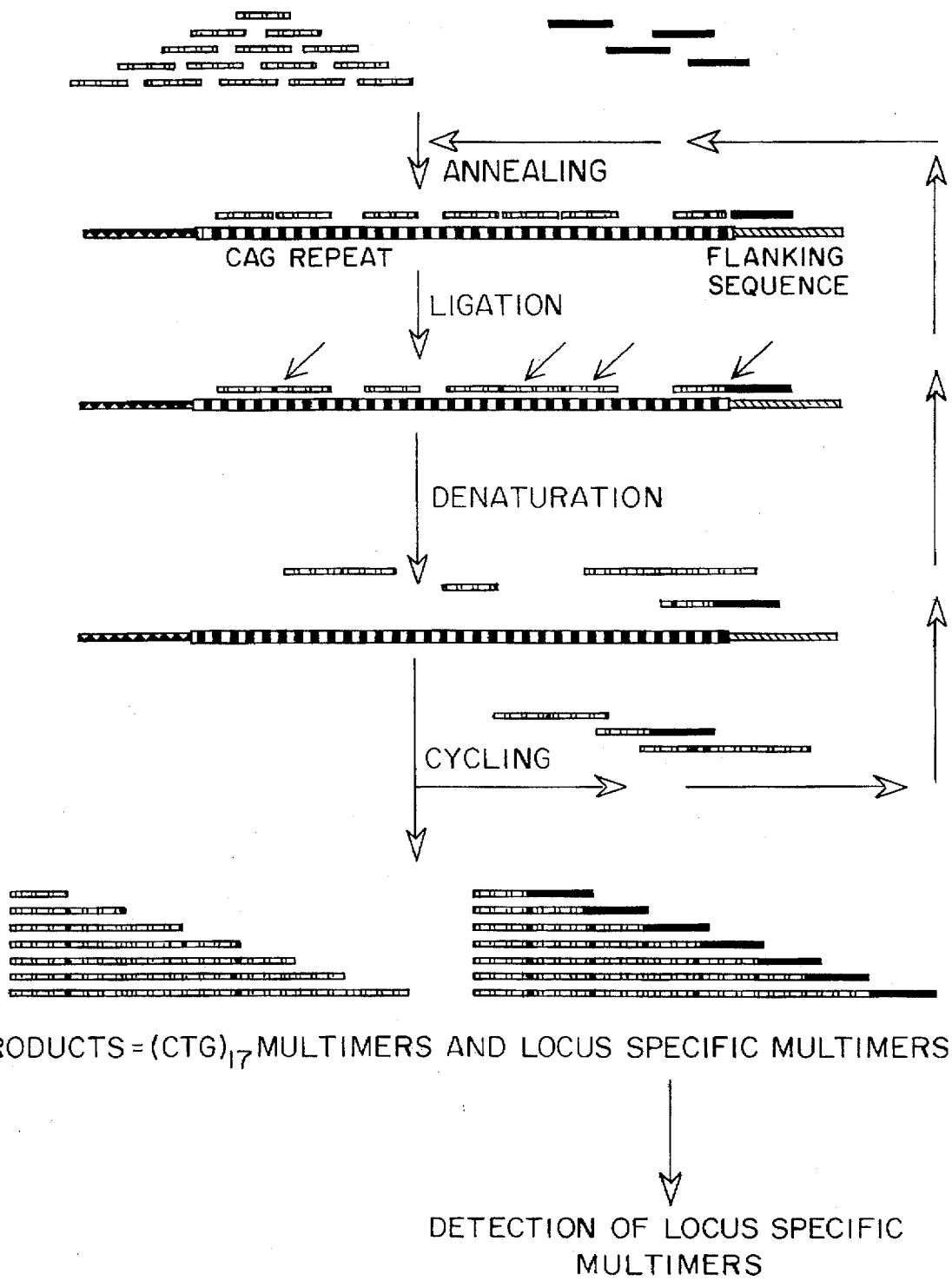
FIG. 3 is a diagram outlining the steps of locus-specific RED using $(CTG)_{17}$ (SEQ ID NO:1) oligonucleotides.

In another embodiment of RED, a specific locus can be assayed for the presence of an expanded repeat sequence. (FIG. 3). In this embodiment, locus-specific oligonucleotides which are not simple sequence repeat oligonucleotides (e.g., nucleic acid sequences which are known to flank the region of an expanded repeat nucleotide present in genomic DNA) and simple sequence repeat oligonucleotides complementary to the nucleotide repeat to be detected are used. They are combined with the genomic DNA to be tested. If an expanded nucleotide repeat is present in the genomic DNA, the simple sequence repeat oligonucleotides anneal to the genomic DNA, as described above. Additionally, if the expanded repeat nucleotide is present in a specific location (e.g., on a specific chromosome) which is flanked (i.e., bordered, or edged) by a nucleotide sequence that is complementary to the locus-specific oligonucleotide, the locus-specific oligonucleotide also anneals to the genomic DNA. Thus, if the expanded repeat nucleotide is located at a specific location of the genomic DNA, the annealing step results in both the simple sequence repeat oligonucleotides and the locus-specific oligonucleotides annealing to the genomic DNA, thus, producing genomic DNA/annealed simple sequence repeat oligonucleotide-locus-specific oligonucleotide complexes.

If only the flanking sequence is present, only the locus-specific oligonucleotide will anneal. If an expanded repeat nucleotide is present, but in a different location (e.g., on a different chromosome or at a different location on a chromosome) than the location defined by (bordered by) the flanking sequence, the simple sequence repeat oligonucleotides will anneal, but not in close proximity to the locus-specific oligonucleotide.

The genomic DNA with annealed oligonucleotides are then ligated as described above using a thermal-stable ligase. In the case where both locus-specific and simple sequence repeat oligonucleotides are annealed to the genomic DNA, the ligation step produces locus-specific multimers of the annealed oligonucleotides (simple sequence repeat multimers containing the locus-specific sequence) in the genomic DNA/annealed oligonucleotide complex. The resulting product is referred to as a genomic DNA/annealed locus-specific multimer complex. If only flanking sequence is present, no ligation occurs. If only expanded repeat nucleotide is present, but not in the expected location (i.e., the location bordered by the flanking sequence), ligation will occur, but the resulting multimers do not include the locus-specific sequence.

The products of the ligation step are then maintained under conditions sufficient for denaturation of the genomic DNA/annealed oligonucleotide complexes, thereby releasing unannealed multimers. If the locus-specific sequence is ligated to simple sequence repeat oligonucleotides, the multimers released are locus-specific multimers. Cycles are repeated until a sufficient number of locus-specific multimers is obtained from detection.

These locus-specific multimers are detected by using labeled oligonucleotide probes complementary to the locus-specific oligonucleotide. The presence of a locus-specific multimer is an indication of the presence of an expanded repeat nucleotide at a specific location in the genomic DNA.

Figure 4:
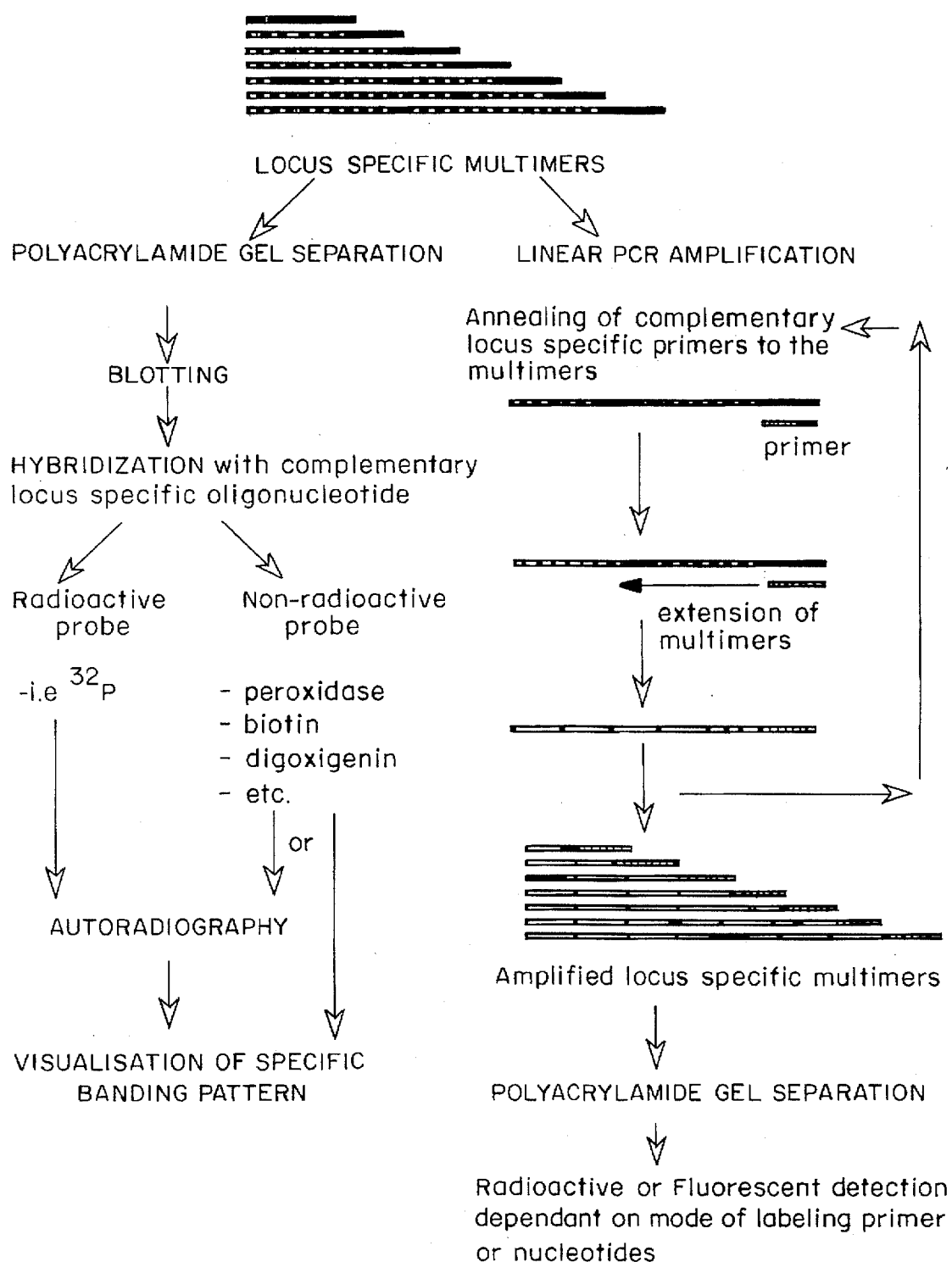
FIG. 4 is a diagram outlining the steps of detection of locus-specific multimers.

These locus-specific multimers can be detected as shown in FIG. 4. In one embodiment, the locus-specific multimers are size-separated by PAGE. In another embodiment, the locus-specific multimers are amplified by linear PCR, using a primer corresponding to the specific locus-specific flanking sequence, before the PAGE, hybridization and visualization steps, to enhance the detection of product multimers. (FIG. 4). In either embodiment, by using a labeled probe complementary to the locus-specific flanking sequence for the hybridization step, multimers can be visualized on the gel at sites unique for the specific locus. Alternately, the primer used in the PCR step can be detectably labeled, e.g., with $^{32}P$ or a fluorescent tag.

RED has been performed using a $(CTG)_{17}$ (SEQ ID NO:1) trinucleotide, with a myotonic dystrophy flanking sequence to detect a (CTG) expanded nucleotide repeat in human genomic DNA. The locus-specific multimers were size-separated by PAGE, blotted, and hybridized with a $^{32}P$-labeled probe complementary to the locus-specific primer sequence. The multimers were then visualized by autoradiography. Faint bands were visible on the gel at the expected positions, evidencing that locus-specific multimers were produced.

Enhanced detection of locus-specific multimers can be accomplished by amplifying the product multimers, such as by using PCR and appropriate sequence-specific primers, as described in Sambrook, J., et al., MOLECULAR CLONING: A LABORATORY MANUAL, 3d Ed., Cold Spring Harbor Laboratory Press (1989). After several rounds of amplification, the copy number of these molecules is increased to allow better sensitivity of detection by radioactive, chemiluminescent and fluorescent means. Thus, RED provides a simple and fast means to detect expanded repeat nucleotides with, or without, prior knowledge of chromosomal location.

The present invention also relates to methods of direct identification of pathological, and potentially pathological repeat expansions in an individual. Four conditions have been identified in which the phenotype is caused by the expansion of a trinucleotide repeat within gene transcripts. In fragile X syndrome (FX), a 5' $(CCG)_n$ repeat found in a brain-expressed gene undergoes sequence amplification in affected individuals. In myotonic dystrophy (MD), a muscle expressed gene was isolated and shown to contain, in its 3' untranslated region, a $(CTG)_n$ repeat which is expanded in myotonic patients. Both disorders are characterized by anticipation (in fragile X syndrome, known as the Sherman paradox) in which successive generations can be more severely affected than the last. In both cases, there is a correlation between repeat size and severity of disease. The size of the repeat involved in disease may vary from approximately 34 to several thousand nucleotide repeats, and there is evidence of somatic mosaicism, particularly with alleles in the high size range (Richards, R. I. and Sutherland, G. R., *Nature Genetics*, 1:7–9 (1991)). For example, in myotonic dystrophy, unaffected individuals have between 5 and 27 repeats of the trinucleotide repeat, CTG (i.e., between 15 and 81 bp). Myotonic dystrophy patients who are minimally affected have at least 50 repeats, while more severely affected patients have expansion of the repeat-containing segment of up to several kilobase pairs. (Brook, J. D., et al., *Cell*, 68:799–808 (1992)).

In addition, spino bulbal muscular atrophy (SBMA, or Kennedy disease) is associated with a (CAG) repeat in the first exon of the androgen receptor. This repeat reaches no more than 200 nucleotides and may vary in size both during transmission and within one individual. (Biancalana, F., et al., *Human Mol. Genet.*, 1:255–258 (1992)). More recently it has been shown that the Huntington's disease gene contains a $(CAG)_n$ repeat. (MacDonald, M. E., et al., *Cell*, 72:971–983 (1993)).

Screening cDNA clones for trinucleotide sequences can be used to identify potential target sites for functionally significant repeat expansion. (Riggins, G. J., et al., *Nature Genetics*, 2:186–191 (1992)). However, this approach requires significant expenditure of labor. The RED method provides an alternate strategy to this labor-intensive approach for identifying clinically significant repeat expansions. It permits the direct visualization of the expanded repeats without prior identification of the genomic site at which the expansion has occurred, providing a direct path for the identification of potentially pathological genes.

Moreover, if the location of the repeat expansion is already known, such as in the case of the above-mentioned pathological conditions, locus-specific RED can be used to as a means of diagnosing these conditions. For example, to diagnose myotonic dystrophy (MD) in an individual, the $(CTG)_{17}$ (SEQ ID NO:1) oligonucleotide, along with known flanking sequences which are complementary to the sequences flanking the expanded CTG repeat in the 3' untranslated region of MD patients, can be used in RED. These oligonucleotides are combined with isolated genomic DNA from an individual, annealed and ligated in repeated cycles to form locus-specific multimers of $(CTG)_{17}$ as described above, and separated by PAGE. After PAGE separation, a labeled probe complementary to the locus-specific primer can be used for hybridization and subsequent visualization of locus-specific multimers.

In a preferred embodiment, the locus-specific multimers are amplified by linear PCR before the PAGE, hybridization and visualization steps, to enhance the detection of product multimers. In either embodiment, the detection of multimers is indicative of the presence of an expanded CTG nucleotide repeat in the 3'0 untranslated region. Determination of the length of the expanded CTG repeat is indicative of whether the individual is affected, or unaffected, by MD, as well as the severity of the condition. For example, if the number of locus-specific CTG nucleotide repeats is less than 10, it is highly unlikely that the individual will be affected by MD. However, if the number is greater than 300, it is highly likely that the individual will be severely affected by MD.

The mechanism by which repeat expansion leads to a biological phenotype remains to be fully elucidated in the cases cited above. In the case of FX it appears likely that repeat expansion leads to inhibition of the transcription of the FMR-1 gene and methylation of surrounding DNA. (Verkerk, A. J., et al., *Cell*, 65:905–914 (1991)). It remains possible for a repeat expansion to have an effect on gene function of clinical significance when located outside the portion of the gene expressed as mRNA. The RED technique would allow such expansions to be detected, whereas a cDNA based assay would not.

Figure 5:
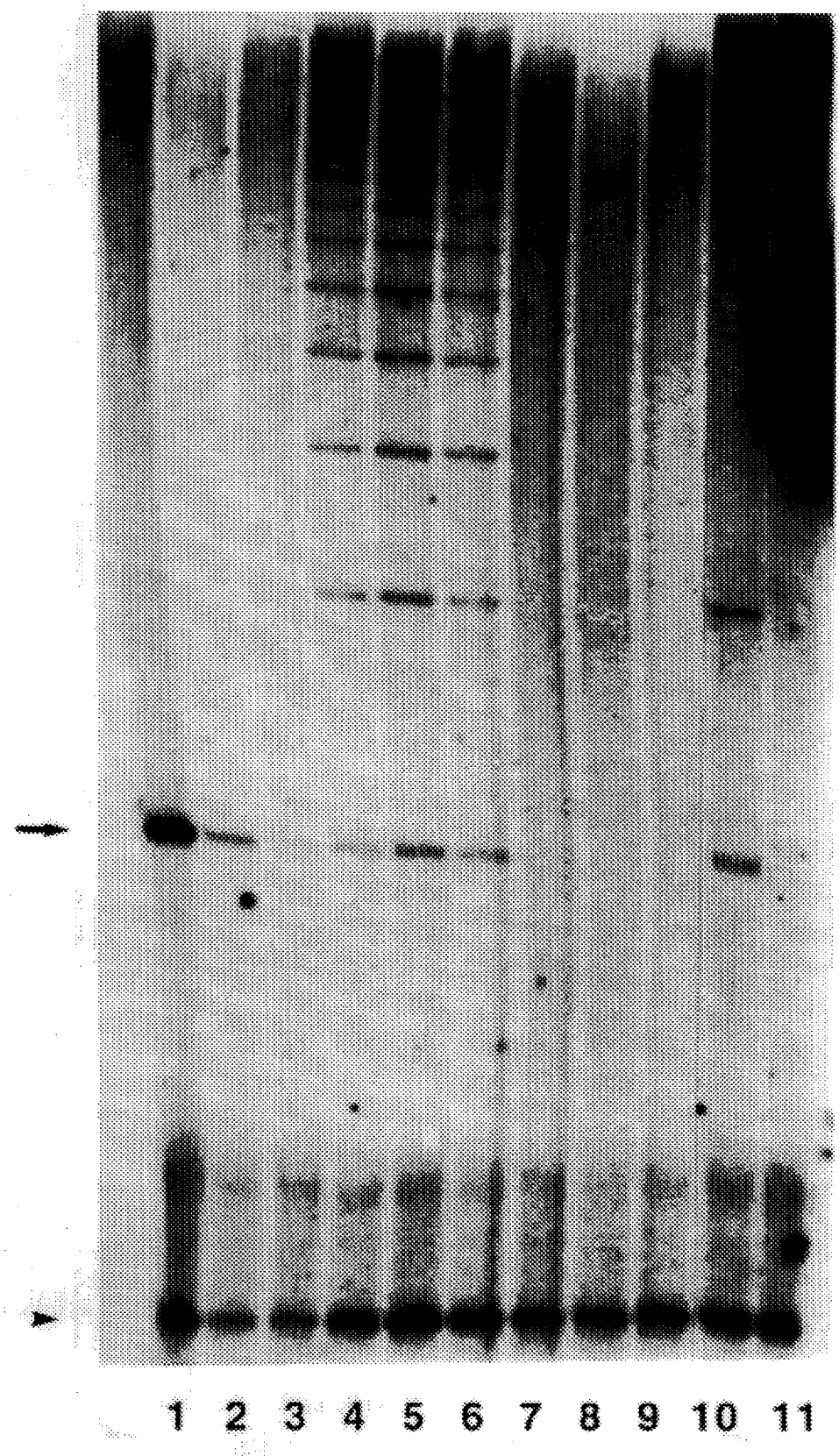
FIG. 5 shows an electrophoretic gel pattern detecting a 141 bp CTG repeat from a mildly affected myotonic dystrophy patient.

The RED technique has permitted the identification of repeat expansions in many individuals. As described in Example 2, genomic DNA from three patients with myotonic dystrophy with known trinucleotide repeat expansion were assayed in the RED method. (FIG. 5, lanes 4–6). In all lanes, products were observed compatible with multimer formation of the original oligonucleotide, ranging from 102 bp to greater than 700 bp.

Figure 6:
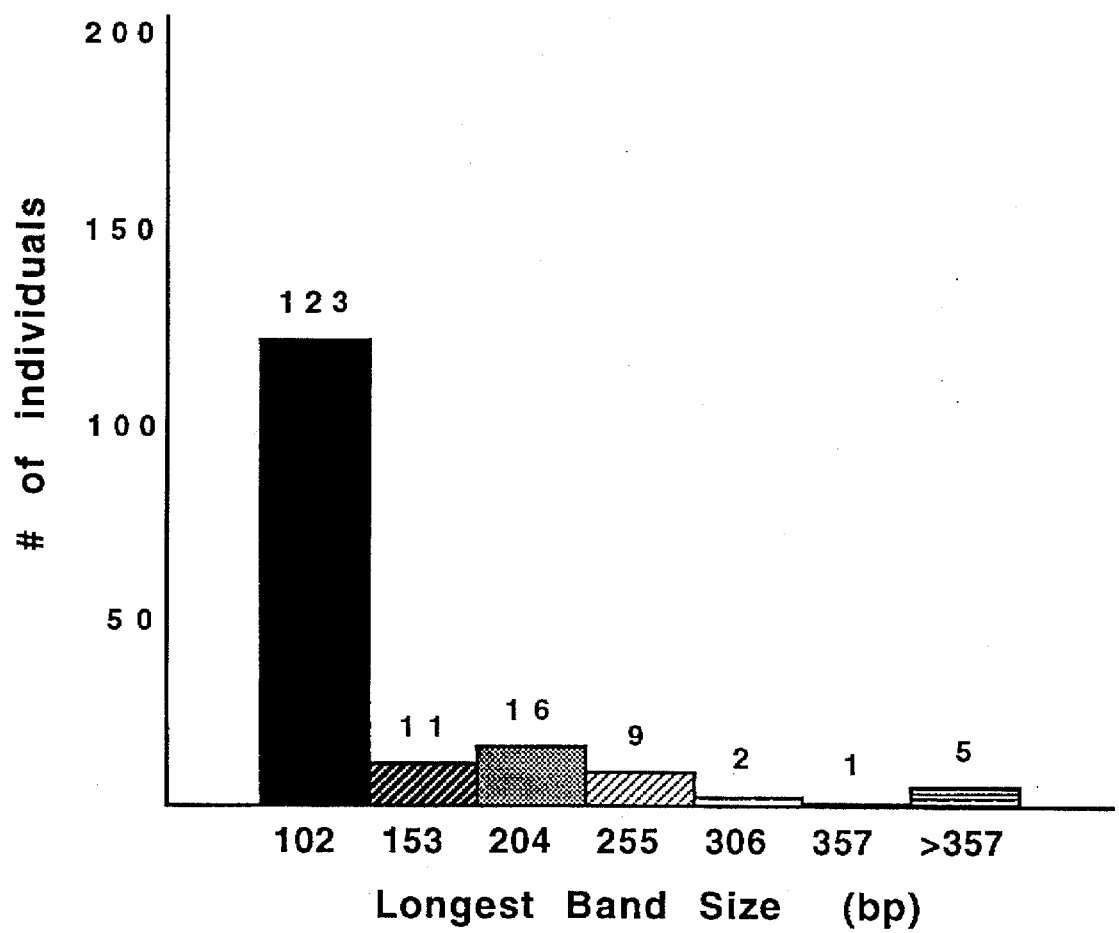
FIG. 6 is a graphic representation of the molecular weight products detected in 168 unrelated individuals.

Also as described in detail in Example 2, genomic DNA from a total of 168 unrelated individuals has been examined using RED and the CTG repeat oligonucleotide. Five individuals with a long CTG repeat were observed (3% of the sample size). Repeats of intermediate size were also observed, with 23% of those examined having products at 153–357 bp and the majority clustered around 204 bp. (FIG. 6).

Figure 7:
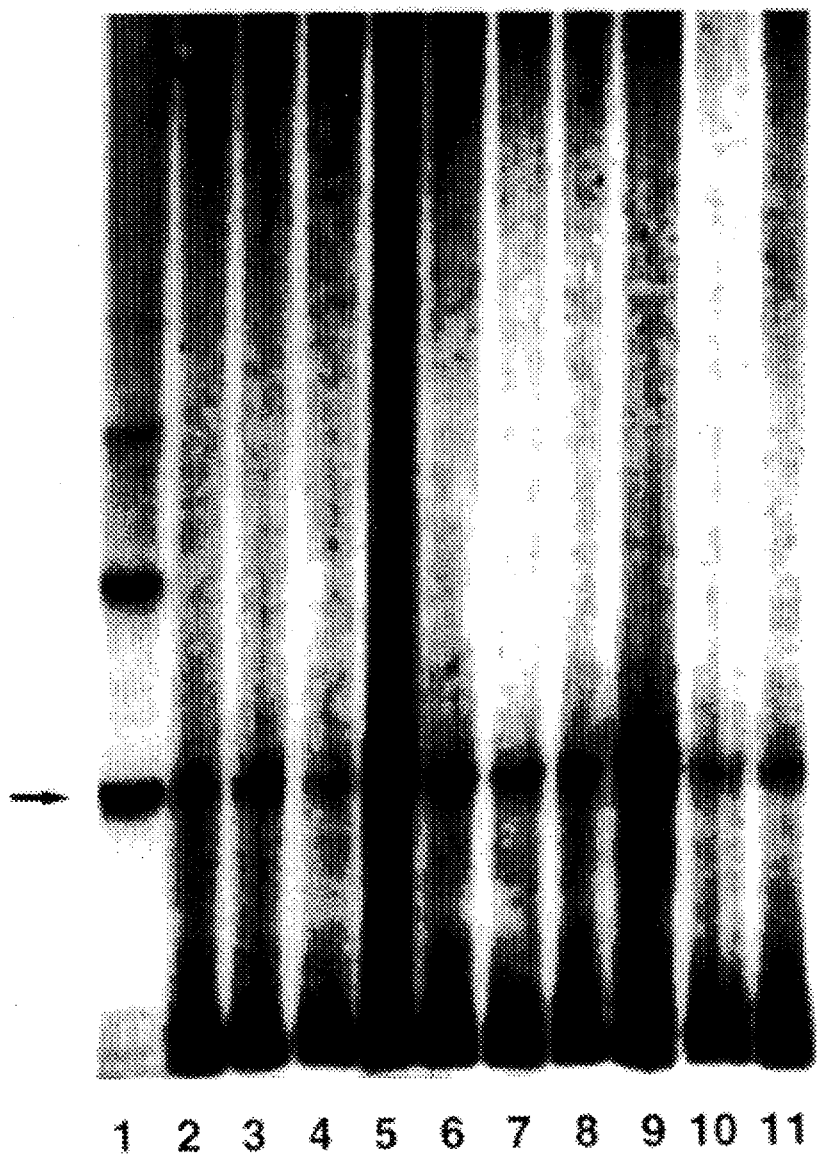
FIG. 7 shows an electrophoretic gel pattern detecting an expanded trinucleotide repeat in a fragile X patient using multiplex RED.

In another embodiment, called "multiplex RED", more than one type of repeat oligonucleotide has been used, as described in detail in Example 3. By combining different types of simple sequence repeat oligonucleotides in one assay, it is possible to simultaneously screen for different expanded nucleotide repeats. The lengths of the single sequence repeat oligonucleotides were chosen so that each type of oligonucleotide had a unique size, thus making possible identification of the respective repeat based on the size of products formed. (FIG. 7)

At present, fragile X DNA can be used as a control to test the efficacy of the CCG ligation reaction, and myotonic dystrophy DNA to test CTG ligation. No expanded repeats have yet been identified with TGG, CCT or CGT as core sequences. However, a population of 168 individuals has been screened for all five repeats as described in Example 3, and shown in FIG. 7. So far only CTG, CCG and CCT products have been detected with a size greater than that corresponding to a single ligation.

Figure 8:
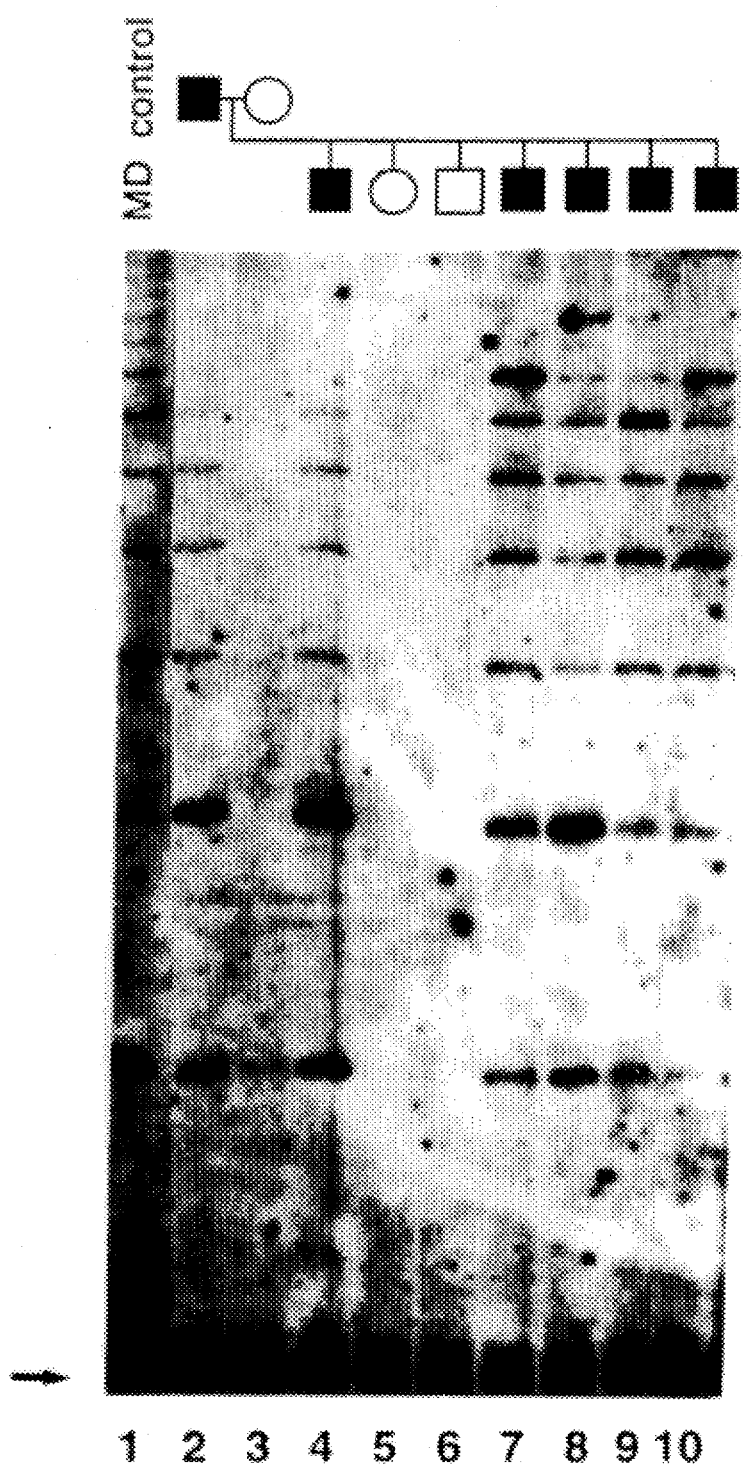
FIG. 8 shows an electrophoretic gel pattern detecting an expanded repeat trinucleotide in genomic DNA from a CEPH family using $(CTG)_{17}$ (SEQ ID NO:1) oligonucleotide.

As described in Example 4, the segregation pattern of two very long repeats and one intermediate repeat from three CEPH (Centre d'Etude du Polymorphisme Humain) pedigrees revealed a pattern of inheritance in all three families consistent with an allele at a single locus (RED-1) on chromosome 18. This result raises the possibility of a founder chromosome giving rise to the repeats in three families or, alternatively, the presence of a locus on chromosome 18 where repeat amplification is particularly common. Interestingly, there was variation in size of the longest product detected within each family. As shown in FIG. 8, the father has 509 bp and the five children have longest products ranging from 560 to 458 bp. Similar variation in the length of the expanded trinucleotide repeat within families has been described in myotonic dystrophy, fragile X syndrome, and spino bulbar muscular atrophy. In these conditions, instability of copy number was observed not only within pedigrees but also within single individuals (somatic mosaicism).

The DNA samples assayed in Example 4 were obtained from cell lines. Thus, the possibility cannot be ruled out that size changes have occurred in vitro as well as in vivo in the pedigrees analyzed. Differences in DNA quality might also influence the size of the longest band detected. However, the longest band seen in any one individual was consistent from experiment to experiment, even when a different DNA preparation was used.

Thus, RED can be used to detect expanded simple sequence repeats from genomic DNA. RED can also be used to investigate the presence of other forms of repeats in the genome. The data presented herein indicates that long trinucleotide repeats occur infrequently in healthy individuals. However, at least one new locus exhibiting trinucleotide expansion has been identified by RED. Analysis of 3 CEPH families transmitting a long CTG repeat shows that the allele in these families corresponds to a locus (RED-1) on chromosome 18. Thus, RED constitutes a powerful tool to identify other diseases caused by this type of mechanism, particularly diseases associated with anticipation.

The present invention also relates to a kit for the diagnosis of a potentially pathological or pathological condition in an individual by the detection of an expanded nucleotide repeat in the genomic DNA of the individual. The kit can include a container of genomic DNA consisting of a known expanded nucleotide repeat sequence to serve as a control. For example, a container of genomic DNA from an individual affected with MD (i.e., having an expanded CTG nucleotide repeat) can be used as a control for the identification of individuals also having an expanded CTG nucleotide repeat in their genomic DNA.

The kit can also include a container of simple sequence repeat oligonucleotides complementary to the expanded repeat nucleotide to be detected in the genomic DNA; a container of labeled oligonucleotide probes which are complementary to the simple sequence repeat oligonucleotide; a container of DNA ligase enzyme in the appropriate concentration; and a container of DNA ligase buffer.

The simple sequence repeat oligonucleotides included with the kit can be one type, or more than one type. For example, they can be $(CGG)_{11}$; $(TGG)_{12}$; $(CCT)_{13}$; $(CGT)_{14}$ (SEQ ID NOS:7–10 respectively); $(CTG)_{17}$, (SEQ ID NOS:1) or any other appropriate simple sequence repeat oligonucleotide complementary to the expanded repeat nucleotide to be detected in the genomic DNA. The labeled oligonucleotide probes can be one type, or more than one type. These can be, for example, $(CCG)_{10}$; $(CCA)_{10}$; $(AGG)_{10}$; $(ACG)_{10}$; $(CAG)_{10}$, (SEQ ID NOS:2–6, respectively) or any other appropriate oligonucleotide probe complementary to the simple sequence repeat oligonucleotide to be detected. The probes can be labeled for example, with $^{32}P$, or with a fluorescent tag.

The present invention will now be illustrated by the following examples, which further and more specifically illustrate the invention.

EXAMPLE 1

RED Detection of an Expanded CTG Repeat from DNA Clone

METHODOLOGY

Sources of genomic DNA, plasmid DNA and oligonucleotides

Human genomic DNA from myotonic dystrophy patients was contributed by Dr. D. Brook. Fragile X patient DNA from Dr. D. Nelson and CEPH DNA from Dr. N. Dracopoli and Dr. V. Stanton. The H7 plasmid containing a 141 bp CTG repeat was contributed by Dr. D. Brook. Oligonucleotides were synthesized by Research Genetics (Huntsville, Ala.) and by the MIT Biopolymers Laboratory. $(CGG)_{11}$, $(TGG)_{12}$, $(CCT)_{13}$, $(CGT)_{14}$ (SEQ ID NOS:7–10 respectively) and $(CTG)_{17}$ (SEQ ID NO:1) oligonucleotides were subsequently purified on a 8% polyacrylamide/6M urea gel. These oligonucleotides were all phosphorylated using dATP and polynucleotide kinase (NEB, Beverly, Mass.) prior to use in the ligation reaction. (Sambrook, J. et al., MOLECULAR CLONING: A LABORATORY MANUAL, 3d Ed., Cold Spring Harbor Press (1989)).

$^{32}$P labeling of oligonucleotides (CCG)$_{10}$, (CCA)$_{10}$, (AGG)$_{10}$, (ACG)$_{10}$ and (CAG)$_{10}$ (SEQ ID NO:2–6 respectively) were 3' end labelled according to the method described in Schalling, M., GENE EXPRESSION IN NEURAL TISSUES, (Ed. Conn, P. M.), Academic Press, Inc., New York, pp. 231–255 (1992) Using terminal deoxynucleotidyl transferase (Bethesda Research Laboratories) and $^{32}$P dATP (NEN 012Z) to a specific activity of 2–9×10$^9$ cpm/ug.

RED reaction conditions

All reactions were performed on a GeneAmp PCR System 9600 (Perkin Elmer Cetus, Norwalk, Conn.) using the following conditions: Reactions (10 or 20 ul) containing 1.0 ug of genomic DNA, 50 ng of phosphorylated oligonucleotide and 5 U of Ampligase (Epicentre Technologies, Madison, Wis.) with the supplied Ampligase buffer were incubated at 94° C. for 5 min. Other standard thermostable ligase/buffers systems, known to those skilled in the art, can also be used. Thereafter, samples were taken through 198 cycles of 80° C. for 90 sec and 94° C. for 10 sec, including a second addition of 5 U Ampligase following 99 cycles.

In some experiments, optional product formation was reached using a shorter time (30 or 60 sec) at 80° C. and increased cycle number (400). The Ampligase remains active up to 500 cycles, or 16 h of cycling.

Electrophoresis and hybridization.

Samples (20 ul) containing 50% formamide, were heat denatured for 5 min before loading on a denaturing polyacrylamide gel. Electrophoresis was performed in a 6% polyacrylamide gel containing 6M urea in a buffer of 100 mM Tris borate, pH 8.1 mM EDTA for 2-,3 hr at 70 W constant power. The gel was transferred to a 3 MM filter paper and the DNA was electrotransferred onto a Hybond N+ membrane using 2 A for 45 min in 1× TBE. Following UV immobilization, the membrane was hybridized for 16 hr at 58° C. to the $^{32}$P labelled oligonucleotide, washed in 1×SSC, 0.1% SDS 1–2 hr at 56° C., and autoradiographed 3–10 days on Fuji X-ray film using an intensifying screen.

Detection of an expanded CTG repeat from a DNA clone

An example of the detection of long repeats using RED is shown in FIG. 5. Initially, the method was tested using a plasmid, H7, derived from an expanded (CTG) repeat. 10 pg, 1 pg, and 100 fg, respectively of a 141 bp CTG repeat from a mildly affected myotonic dystrophy patient was cloned in Bluescript mixed with 1 ug of genomic DNA as a carrier. (FIG. 5, lanes 1–3). All samples included 50 ng of phosphorylated (CTG)$_{17}$ (SEQ ID NO:1) oligonucleotide and were cycled 198 times at 94°/80° C. with addition of 5 U of Ampligase initially, and following 99 cycles.

In lane 1 of FIG. 5 (10 pg of the H7 clone) products are observed at both 102 and 153 bp corresponding to coligation of two and three oligonucleotides respectively. Using 1 pg (lane 2), or 100 fg (lane 3), in the reaction results in progressively less product detected, indicating that the reaction is substrate dependent. (The arrow in FIG. 5 denotes 153 bp product, the arrow head denotes 102 bp product).

The ligation strategy was also tested using 1 pg H7 clone with a 30 base CTG repeat oligonucleotide. After 198 cycles of 80° C. and 95° C., bands were seen at 90, 120 and 150 nucleotides in size corresponding to two, three and four ligations respectively (not shown). A high concentration (100 pg) of H7 gave rise to additional bands at 180, 210 and 240 nucleotides, but with a much reduced intensity compared to the 150 nucleotide band (not shown). This is interesting in light of the repeat size contained in the H7 clone, which is 141 bp. It thus appears that a limited number of products (i.e., annealed multimers) can be formed which are of greater size than the template used, most likely due to a second annealing of already ligated molecules.

EXAMPLE 2

Detection of Expanded CTG Repeats in Genomic DNA

Genomic DNA (1 ug) from three patients with myotonic dystrophy and known trinucleotide expansion within the MD-1 gene was also tested using the method described in Example 1 (FIG. 5, lanes 4–6). In all lanes, multiple products are observed with sizes compatible with multimer formation of the original oligonucleotide, ranging from 102 bp to greater than 700 bp. Using Southern blotting and a probe specific for the MD-1 locus, it was shown that the repeat size in all three individuals was higher then 800 bp.

A sample of unrelated individuals (FIG. 5, lanes 7–11) demonstrates a product at 102 bp in all cases. In addition, one individual (lane 10) shows products at 153 and 204 bp. Genomic DNA from a total of 168 unrelated individuals using RED and the CTG repeat oligonucleotide have been examined. A summary of the highest molecular weight product detected in these individuals is shown in FIG. 6. The 357 bp group includes all individuals with a ladder of products, sometimes resolvable to 1000 bp in size. The 102 bp product was used as an indicator that ligation occurred in each reaction, most likely from the annealing of the oligonucleotide to multiple short CAG repeats in the genome where size permits only a single ligation. Only individuals with a clear 102 bp product as a sign of successful ligation were included in FIG. 6. In 123 of 168 (73%) individuals, no products of higher molecular weight were observed, suggesting the absence of long CAG repeats in their genome. In five individuals, product longer than 350 bp were seen, forming a ladder of multiple products similar to what was observed in the DNA of myotonic dystrophy patients (FIG. 5, lanes 4–6). Intermediate size products were observed In 39 Individuals (23%)(FIG. 6). An example of such an individual is shown in FIG. 5, lane 10.

EXAMPLE 3

Multiplex RED

To expand the capacity of RED to reveal expansions in other repeat sequence formulas, a strategy was devised for multiplex RED assays for different trinucleotide repeats. Four different repeat oligonucleotides were used together in the ligase reaction. To differentiate between products formed by each type of repeat, oligonucleotides were synthesized in different sizes: (CGG)$_{11}$, (TGG)$_{12}$, (CCT)$_{13}$, (CGT)$_{14}$ (SEQ ID NOS:7–10 respectively) and (CTG)$_{17}$ (SEQ ID NO:1).

Following thermal cycling with any four of the above oligonucleotides, and electrophoresis, membranes were hybridized with a mixture of four complementary oligonucleotides, each 30 nucleotide long. As a positive control for the multiplex RED assay, DNA from a fragile X mental retardation patient was used (FIG. 7, lane 1). Products were observed at 99, 132, 165 and 198 bp, consistent with a formation of multimers of the (CGG)$_{11}$ (SEQ ID NO:7) oligonucleotide. This oligonucleotide is complementary to one of the strands within the repeat present in the FMR-1 gene of the tested fragile X patient.

Ten control individuals are shown in FIG. 7, lanes 2–11, displaying only a faint band at 99 bp, compatible with a limited degree of trimer formation in normal individuals. (Arrow denotes 99 bp product). Over 150 individuals have been tested for the presence of long CGG, TGG, CCT and CGT repeats using RED. No individuals surveyed showed any CCG product beyond 99 bp.

Using the CCT oligonucleotide, products were observed at 117, 156 and 195 bp in four individuals. No products were seen with TGG and CGT. In total, ten unrelated individuals with multiple RED products consistent with the presence of a long trinucleotide repeat in their respective genomes have been identified. Further analysis should determine if these repeats are possibly correlated with genetic disease.

EXAMPLE 4

A Novel Expanded CTG Repeat on Human Chromosome 18

Three of the individuals with multiple products were parents in Centre d'Etude du Polymorphisme Humain (CEPH) pedigrees, permitting analysis of inheritance. A pattern consistent with a Mendelian mode of inheritance of a single locus was observed in all three families. In FIG. 8, CEPH family 1334 has been assayed by RED using a CTG oligonucleotide. In lane 1 genomic DNA from a myotonic dystrophy patient is included as a reference. The pedigree of CEPH family 1334 is depicted above lanes 2–14, with individuals giving rise to products above 306 bp marked in black. (Arrow denotes 102 bp).

A ladder is observed in the father and five of seven children. The size of the largest product varied within members of the same family. For example, the son in lane 7 displays 459 bp as the longest product, whereas the son in lane 8 has two additional products, reaching 561 bp. Two other CEPH families (1344 and 1420) showed transmission of a long CTG repeat (figures not shown). Variability in the size of the longest product was also observed in both of these families, with family 1344 varying between 306 and 357, and family 1420 varying between 306 and greater than 816 bp.

Linkage analysis was performed to investigate whether the long CTG repeats segregating in these families could represent a single locus. A carrier was defined as an individual with a longest product at or above 300 bp. Two-point linkage analysis to markers in the CEPH database (version 5) was conducted. Positive LOD scores were seen for markers located on chromosome 18. Additional genotyping of these three families was performed with tetranucleotide repeat MIT-T38. MIT-T38 was previously mapped to chromosome 18 using the NIGMS human/rodent somatic cell hybrid mapping panel 1. This marker was informative in all three families. Two-point linkage analysis revealed a LOD-score of 3.41 at 10 cM suggesting that the expanded repeat in these three families might indeed be on chromosome 18. The MD-1 locus has been excluded as the site of repeat expansion in these families by demonstrating normal sized alleles using PCR with primers 101 and 102 (Brook, J. D., et al., *Cell*, 68:799–808 (1992)).

Equivalents

Those skilled in the art will recognize, or be able to ascertain, using no more than routine experimentation, many equivalents to the specific embodiments of the invention described herein.

---

The invention claimed is:

1. A method of detecting an expanded nucleotide repeat of undetermined length in genomic DNA in a biological sample, comprising the steps of:
   (a) isolating genomic DNA contained in a biological sample, thereby producing isolated genomic DNA;
   (b) combining genomic DNA from step (a) with immediately ligatable simple sequence repeat oligonucleotides consisting of a nucleic acid sequence complementary to a nucleotide repeat to be detected in the genomic DNA, thereby producing a combination of genomic DNA and immediately ligatable oligonucleotides;
   (c) annealing the immediately ligatable oligonucleotides to the isolated genomic DNA, thereby producing genomic DNA/annealed oligonucleotide complexes;
   (d) ligating the annealed oligonucleotides to produce multimers of the annealed oligonucleotides in the genomic DNA/annealed oligonucleotide complexes, thereby producing genomic DNA/annealed multimer complexes;
   (e) denaturing the genomic DNA/annealed multimer complexes, thereby releasing the annealed multimers from the multimer complexes and producing unannealed multimers; and
   (f) repeating steps (c) through (e) to obtain a sufficient number of unannealed multimers for detection, whereby the presence of unannealed multimers is an indication of the presence of an expanded nucleotide repeat in the genomic DNA.

2. The method of claim 1 wherein the method further comprises the steps of:

(g) separating, on the basis of size, unannealed multimers by polyacrylamide gel electrophoresis;

(h) electrotransferring the gel from step (g) to a membrane suitable for hybridization thereby producing a membrane having present thereon unannealed multimers;

(i) contacting labeled oligonucleotide probes, having nucleic acid sequences complementary to the unannealed multimers, with the membrane produced in step (h) under conditions sufficient for hybridization of the labeled oligonucleotide probes to the unannealed multimers present on the membrane, whereby labeled oligonucleotide probes and unannealed multimers hybridize, thereby producing a pattern of labeled probes hybridized to unannealed multimers; and (j) visualizing the pattern of labeled oligonucleotide probes hybridized to the unannealed multimers present on the membrane, whereby the visualized pattern is an indication of the presence and size of unannealed multimers.

3. The method of claim 1 wherein the simple sequence repeat oligonucleotides provided in step (b) are labelled with a florescent tag.

4. The method of claim 2 wherein the oligonucleotide probes of step (i) are labeled with a radioactive label and the visualization step (j) is by autoradiography.

5. The method of claim 2 wherein the oligonucleotide probes of step (i) are labelled with a non-radioactive label.

6. The method of claim 4 wherein the radioactive label is $^{32}$P.

7. The method of claim 5 wherein the non-radioactive label is peroxidase, biotin or digoxigenin.

8. The method of claim 3 wherein the method further comprises the steps of:

(g) separating, on the basis of size, unannealed multimers tagged with a florescent tag by polyacrylamide gel electrophoresis;

(h) detecting the presence of florescent-tagged unannealed multimers in the gel of step (g) using a fluorescence-detecting scanner.

9. A method of detecting an expanded trinucleotide repeat of undetermined length in genomic DNA in a biological sample, comprising the steps of:

(a) isolating genomic DNA contained in a biological sample, thereby producing isolated genomic DNA;

(b) combining genomic DNA from step (a) with immediately ligatable simple sequence repeat oligonucleotides consisting of a nucleic acid sequence complementary to the trinucleotide repeat to be detected in the genomic DNA, thereby producing a combination of genomic DNA and immediately ligatable oligonucleotides;

(c) annealing the immediately ligatable oligonucleotides to the isolated genomic DNA, thereby producing genomic DNA/annealed oligonucleotide complexes;

(d) ligating the annealed oligonucleotides to produce multimers of the annealed oligonucleotides in the genomic DNA/annealed oligonucleotide complex, thereby producing genomic DNA/annealed multimer complexes;

(e) denaturing the genomic DNA/annealed multimer complexes, thereby releasing the annealed multimers from the multimer complexes and producing unannealed multimers;

(f) repeating steps (c) through (e) to obtain a sufficient number of unannealed multimers for detection;

(g) separating, on the basis of size, unannealed multimers by polyacrylamide gel electrophoresis;

(h) electrotransferring the gel from step (g) to a membrane suitable for hybridization, thereby producing a membrane having present thereon unannealed multimers;

(i) contacting radiolabeled oligonucleotide probes having nucleic acid sequences complementary to the unannealed multimers with the membrane produced in step (h), under conditions sufficient for hybridization of the radiolabeled oligonucleotide probes to the unannealed multimers present on the membrane, whereby radiolabeled oligonucleotide probes and unannealed multimers hybridize, thereby producing radiolabeled probes hybridized to unannealed multimers; and (j) visualizing, by autoradiography, radiolabeled oligonucleotide probes hybridized to the unannealed multimers whereby visualized radiolabeled probes are an indication of the presence of unannealed multimers and the presence of unannealed multimers is an indication of the presence of an expanded trinucleotide repeat in the genomic DNA.

10. The method of claim 9 wherein the radioactive label is $^{32}$P.

11. The method of claim 9 wherein the simple sequence repeat oligonucleotides provided in step (b) are one or more selected from the group consisting of:

(CGG)$_{11}$; (TGG)$_{12}$; (CCT)$_{13}$; (CGT)$_{14}$ (SEQ ID NOS:7–10) and (CTG)$_{17}$ (SEQ ID NO:1) and the labeled oligonucleotide probes of step (i) are one or more selected from the group consisting of: (CCG)$_{10}$; (CCA)$_{10}$; (AGG)$_{10}$; (ACG)$_{10}$ and (CAG)$_{10}$ (SEQ ID NOS:2–6).

12. A method of detecting a locus-specific expanded nucleotide repeat of undetermined length in genomic DNA in a biological sample, comprising the steps of:

(a) isolating genomic DNA contained in a biological sample, thereby producing isolated genomic DNA;

(b) combining the genomic DNA from step (a) with immediately ligatable simple sequence repeat oligonucleotides consisting of a nucleic acid sequence complementary to the nucleotide repeat to be detected in the genomic DNA, and with immediately ligatable oligonucleotides consisting of a nucleic acid sequence complementary to a nucleic acid sequence located at a specific locus on the genomic DNA, thereby producing a combination of genomic DNA, immediately ligatable simple sequence repeat oligonucleotides and immediately ligatable locus-specific oligonucleotides;

(c) annealing the immediately ligatable simple sequence repeat oligonucleotides and immediately ligatable locus-specific oligonucleotides to the isolated genomic DNA, thereby producing genomic DNA/annealed locus-specific oligonucleotide complexes;

(d) ligating the annealed oligonucleotides to produce multimers of the annealed oligonucleotides in the genomic DNA/annealed locus-specific oligonucleotide complexes, thereby producing genomic DNA/annealed locus-specific multimer complexes;

(e) denaturing the genomic DNA/annealed locus-specific multimer complexes, thereby releasing annealed locus-specific multimers from the multimer complexes and producing unannealed locus-specific multimers;

(f) repeating steps (c) through (e) to obtain a sufficient number of unannealed locus-specific multimers for detection, whereby the presence of unannealed locus-specific multimers is an indication of the presence of an expanded nucleotide repeat located at a specific locus on the genomic DNA.

13. The method of claim 12 wherein the method further comprises the steps of:
   (g) separating, on the basis of size, unannealed locus-specific multimers by polyacrylamide gel electrophoresis;
   (h) electrotransferring the gel from step (g) to a membrane suitable for hybridization thereby producing a membrane having present thereon unannealed locus-specific multimers;
   (i) contacting labeled oligonucleotide probes having nucleic acid sequences complementary to the locus-specific unannealed multimers with the membrane produced in step (h) under conditions sufficient for hybridization of the labeled oligonucleotide probes to the unannealed locus-specific multimers present on the membrane, whereby labeled oligonucleotide probes and unannealed multimers hybridize, thereby producing labeled probes hybridized to unannealed locus-specific multimers; and
   (j) visualizing the labeled oligonucleotide probes hybridized to the unannealed locus-specific multimers present on the membrane, whereby visualized labeled probes are an indication of the presence of unannealed locus-specific multimers and the presence of unannealed locus-specific multimers is an indication of the presence of a locus-specific expanded nucleotide repeat in the genomic DNA.

14. The method of claim 12 wherein the simple sequence repeat oligonucleotides provided in step (b) are labelled with a florescent tag.

15. The method of claim 12 further comprising the steps:
   (g) amplifying the unannealed locus-specific multimers using linear PCR and primers;
   (h) separating, on the basis of size, amplified unannealed locus-specific multimers by polyacrylamide gel electrophoresis;
   (i) electrotransferring the gel from step (h) to a membrane suitable for hybridization thereby producing a membrane having present thereon unannealed locus-specific multimers;
   (j) contacting labeled oligonucleotide probes having nucleic acid sequences complementary to unannealed locus-specific multimers with the membrane produced in step (i) under conditions sufficient for hybridization of the labeled oligonucleotide probes to the unannealed locus-specific multimers present on the membrane, whereby labeled oligonucleotide probes and unannealed locus-specific multimers hybridize, thereby producing labeled probes hybridized to unannealed locus-specific multimers; and
   (k) visualizing the labeled oligonucleotide probes hybridized to the unannealed locus-specific multimers membrane, whereby visualized labeled probes are an indication of the presence of unannealed locus-specific multimers and the presence of unannealed locus-specific multimers is an indication of the presence of a locus-specific expanded nucleotide repeat.

16. The method of claim 13 wherein the oligonucleotide probes of step (i) are labeled with a radioactive label and the visualization step (j) is by autoradiography.

17. The method of claim 13 wherein the oligonucleotide probes of step (i) are labelled with a non-radioactive label.

18. The method of claim 16 wherein the radioactive label is $^{32}$P.

19. The method of claim 17 wherein the non-radioactive label is peroxidase, biotin or digoxigenin.

20. The method of claim 14 wherein the method further comprises the steps of:
   (g) separating, on the basis of size, unannealed locus-specific multimers tagged with a florescent tag by polyacrylamide gel electrophoresis;
   (h) detecting the presence of florescent-tagged unannealed locus-specific multimers in the gel of step (g) using a fluorescence-detecting scanner.

21. The method of claim 15 wherein the oligonucleotide probes of step (j) are labeled with a radioactive label and the visualization step (k) is by autoradiography.

22. The method of claim 15 wherein the oligonucleotide probes of step (j) are labeled with a florescent tag and the visualization step (k) is by detecting the presence of florescent-tagged probes using a fluorescence-detecting scanner.

23. The method of claim 21 wherein the radioactive label is $^{32}$P.

24. A method of detecting an expanded nucleotide repeat of undetermined length in genomic DNA in a biological sample, comprising the steps of:
   (a) isolating genomic DNA from a biological sample;
   (b) combining the genomic DNA from step (a) with a mixture of different types of immediately ligatable simple sequence repeat oligonucleotides, each type of oligonucleotide consisting of a nucleic acid sequence complementary to a different type of nucleotide repeat to be detected in the genomic DNA, thereby producing a combination of genomic DNA and immediately ligatable oligonucleotides;
   (c) annealing the different types of immediately ligatable simple sequence repeat oligonucleotides to the isolated genomic DNA, thereby producing genomic DNA/annealed oligonucleotide complexes;
   (d) ligating the annealed oligonucleotides to produce multimers of the annealed oligonucleotides in the genomic DNA/annealed oligonucleotide complexes, thereby producing genomic DNA/annealed multimer complexes;
   (e) denaturing the genomic DNA/multimer complexes thereby releasing annealed multimers and producing unannealed multimers;
   (f) repeating steps (c) through (e) to obtain a sufficient number of unannealed multimers for detection;
   (g) separating, on the basis of size, unannealed multimers by polyacrylamide gel electrophoresis;
   (h) electrotransferring the gel from step (g) to a membrane suitable for hybridization thereby producing a membrane having present thereon unannealed multimers;
   (I) contacting a mixture of different types of radiolabeled oligonucleotide probes having nucleic acid sequences complementary to the unannealed multimers with the membrane produced in step (h) under conditions sufficient for hybridization of the radiolabeled oligonucleotide probes to the unannealed multimers present on the membrane whereby radiolabeled oligonucleotide probes and unannealed multimers hybridize, thereby producing a pattern of radiolabeled probes hybridized to unannealed multimers; and
   (j) visualizing the pattern of radiolabeled oligonucleotide probes hybridized to the unannealed multimers present on the membrane by autoradiography, whereby the visualized pattern is an indication of the presence and size of unannealed multimers and the presence and size of unannealed multimers is an indication of the presence of a type of expanded nucleotide repeat in the genomic DNA.

25. The method of claim 24 wherein the radioactive label is $^{32}$P.

26. The method of claim 24 wherein the simple sequence repeat oligonucleotides provided in step (b) are one or more selected from the group consisting of:

(CGG)$_{11}$; (TGG)$_{12}$; (CCT)$_{13}$; (CGT)$_{14}$ (SEQ ID NOS.:7–10) and (CTG)$_{17}$ (SEQ ID NO.:1) and the labeled oligonucleotide probes of step (i) are one or more selected from the group consisting of: (CCG)$_{10}$; (CCA)$_{10}$; (AGG)$_{10}$; (ACG)$_{10}$ and (CAG)$_{10}$; (SEQ ID NOS.:2–6).

27. A method of diagnosing a potentially pathological or pathological condition in an individual by the detection of a locus-specific expanded nucleotide repeat of undetermined length characteristic of the condition in the genomic DNA of the individual comprising the steps of:

(a) isolating genomic DNA from a biological sample;

(b) combining the genomic DNA from step (a) with immediately ligatable simple sequence repeat oligonucleotides consisting of a nucleic acid sequence complementary to the nucleotide repeat characteristic of the condition to be detected in the genomic DNA, and immediately ligatable oligonucleotides consisting of a nucleic acid sequence complementary to a nucleic acid sequence located at a specific locus on the genomic DNA, thereby producing a combination of DNA, immediately ligatable simple sequence repeat oligonucleotides and immediately ligatable locus-specific oligonucleotides;

(c) annealing the immediately ligatable simple sequence repeat oligonucleotides and the immediately ligatable locus-specific oligonucleotides to the isolated genomic DNA, thereby producing genomic DNA/annealed locus-specific oligonucleotide complexes;

(d) ligating the annealed oligonucleotides to produce multimers of the annealed oligonucleotides in the genomic DNA/annealed locus-specific oligonucleotide complexes, thereby producing genomic DNA/annealed locus-specific multimer complexes;

(e) denaturing the genomic DNA/annealed locus-specific multimer complexes, thereby releasing annealed locus-specific multimers and producing unannealed locus-specific multimers;

(f) repeating steps c through (e) to obtain a sufficient number of unannealed locus-specific multimers for detection;

(g) amplifying the unannealed locus-specific multimers using linear PCR and primers;

(h) separating, on the basis of size, amplified unannealed locus-specific multimers by polyacrylamide gel electrophoresis;

(I) electrotransferring the gel from step (h) to a membrane suitable for hybridization thereby producing a membrane having present thereon unannealed locus-specific multimers;

(j) contacting labeled oligonucleotide probes having nucleic acid sequences complementary to the locus-specific unannealed multimers with the membrane produced in step (I) under conditions sufficient for hybridization of the labeled oligonucleotide probes to the unannealed locus-specific multimers present on the membrane, thereby providing labeled probes hybridized to unannealed locus-specific multimers; and (k) visualizing the labeled oligonucleotide probes hybridized to the unannealed locus-specific multimers present on the membrane, whereby visualized labeled probes are an indication of the presence of unannealed locus-specific multimers and the presence of unannealed locus-specific multimers is an indication of the presence of a locus-specific expanded nucleotide repeat characteristic of a potentially pathological or pathological condition.

28. The method of claim 27 wherein the oligonucleotide probes of step (j) are labeled with a radioactive label and the visualization step (k) is by autoradiography.

29. The method of claim 28 wherein the radioactive label is $^{32}$P.

30. A kit for the diagnosis of a potentially pathological or pathological condition in an individual by the detection of an expanded nucleotide repeat of undetermined length in the genomic DNA of the individual comprising:

(a) a container of genomic DNA consisting of a known expanded nucleotide repeat sequence;

(b) a container of simple sequence repeat oligonucleotides;

(c) a container of labeled oligonucleotide probes;

(d) a container of DNA ligase enzyme; and (e) a container of DNA ligase buffer.

31. A kit for the diagnosis of a potentially pathological or pathological condition in an individual by the detection of an expanded nucleotide repeat of undetermined length in the genomic DNA of the individual comprising:

(a) a container of genomic DNA consisting of a known expanded nucleotide repeat sequence;

(b) a container of one or more simple sequence repeat oligonucleotides selected from the group consisting of: (CGG)$_{11}$; (TGG)$_{12}$; (CCT)$_{13}$; (CGT)$_{14}$ (SEQ ID NOS.:7–10) and (CTG)$_{17}$; (SEQ ID NO.:1);

(c) a container of one or more labeled oligonucleotide probes selected from the group consisting of: (CCG)$_{10}$; (SEQ ID NOS.:2–6); (CCA)$_{10}$; (AGG)$_{10}$; (ACG)$_{10}$ and (CAG)$_{10}$;

(d) a container of DNA ligase enzyme; and (e) a container of DNA ligase buffer.

32. The kit of claim 31 wherein the labeled oligonucleotide probes are labeled with $^{32}$P.

33. The kit of claim 31 wherein the labeled oligonucleotide probes are labeled with a florescent tag.

34. A method of identifying an expanded nucleotide repeat of undetermined length in genomic DNA in a biological sample which is characteristic of a genetic condition in an individual comprising the steps of:

(a) isolating genomic DNA from a biological sample;

(b) combining the genomic DNA from step (a) with immediately ligatable simple sequence repeat oligonucleotides consisting of a nucleic acid sequence complementary to the nucleotide repeat to be detected in the genomic DNA, thereby producing a combination of genomic DNA and immediately ligatable oligonucleotides;

(c) annealing the immediately ligatable oligonucleotides to the isolated genomic DNA, thereby producing genomic DNA/annealed oligonucleotide complexes;

(d) ligating the annealed oligonucleotides to produce multimers of the annealed oligonucleotides in the genomic DNA/annealed oligonucleotide complex, thereby producing genomic DNA/annealed multimer complexes;

(e) denaturing the genomic DNA/annealed multimer complexes, thereby releasing the annealed multimers from the multimer complexes and producing unannealed multimers;

(f) repeating steps (c) through (e) to obtain a sufficient number of unannealed multimers for detection;

(g) separating, on the basis of size, unannealed multimers by polyacrylamide gel electrophoresis;

(h) electrotransferring the gel from step (g) to a membrane suitable for hybridization, thereby producing a membrane having present thereon unannealed multimers;

(I) contacting labeled oligonucleotide probes having nucleic acid sequences complementary to the unannealed multimers with the membrane produced in step (h), under conditions sufficient for hybridization of the labeled oligonucleotide probes to the unannealed multimers present on the membrane, whereby label oligonucleotide probes and unannealed multimers hybridize, thereby producing labeled probes hybridized to unannealed multimers; and (j) visualizing labeled oligonucleotide probes hybridized to the unannealed multimers whereby visualized labeled probes are an indication of the presence unannealed multimers and the presence of unannealed multimers is an indication of the presence of an expanded nucleotide repeat in the genomic DNA which is characteristic of a genetic condition in an individual.

35. A method of detecting the presence of and determining the length of an expanded nucleotide repeat in genomic DNA, comprising the steps of:

a) providing multiple copies of immediately ligatable repeat-specific oligonucleotides consisting of a nucleic acid sequence complementary to the expanded nucleotide repeat to be detected;

b) annealing the multiple copies of immediately ligatable repeat-specific oligonucleotides to the expanded nucleotide repeat, if present in the genomic DNA, to form repeat-specific oligonucleotide/expanded nucleotide repeat complexes comprising two, or more, adjacent repeat-specific oligonucleotides annealed to the expanded nucleotide repeat;

c) ligating two or more adjacent repeat-specific oligonucleotides present in the complex with a thermostable ligase to form multimers of various lengths of the annealed repeat-specific oligonucleotides;

d) denaturing the complexes to release the multimers from the genomic DNA;

e) repeating steps b) through d) to form multimers of maximum length and in sufficient number for detection; and f) separating the multimers of various lengths on the basis of size and detecting the multimers wherein the longest length of multimer detected is indicative of the length of the expanded nucleotide repeat present in the genomic DNA.

36. The method of claim 35 wherein the repeat-specific oligonucleotides are one or more selected from the group consisting of: $(CGG)_{11}$; $(TGG)_{12}$; $(CCT)_{13}$; $(CGT)_{14}$ (SEQ ID NOS.:7-10) and $(CTG)_{17}$ (SEQ ID NO.:1).

37. The method of claim 35 wherein the separation of multimers on the basis of size comprises separation by polyacrylamide gel electrophoresis and the detection of multimers comprises the following steps:

a) electrotransferring the gel to a membrane suitable for hybridization, thereby producing a membrane having present thereon multimers of various lengths;

b) providing labeled oligonucleotide probes having nucleic acid sequences complementary to the multimers to be detected;

c) contacting the labeled oligonucleotide probes with the membrane of step a) under conditions sufficient for hybridization of the labeled probes to the multimers present on the membrane, whereby labeled probes hybridize to the multimers thereby producing a pattern of labeled probed hybridized to the multimers of various lengths; and d) visualizing the pattern of labeled probes hybridized to the multimers present on the membrane, whereby the visualized pattern is an indication of the presence and length of multimers.

38. The method of claim 35 wherein the repeat-specific oligonucleotides are labeled whir a fluorescent tag.

39. The method of claim 37 wherein the labeled oligonucleotide probes are one or more selected from the group consisting of: $(CCG)_{10}$; $(CCA)_{10}$; $(AGG)_{10}$; $(ACG)_{10}$ and $(CAG)_{10}$ (SEQ ID NOS.:2–6).

40. The method of claim 37 wherein the labeled oligonucleotide probes are labeled with a radioactive label and the visualization step is accomplished by autoradiography.

41. The method of claim 37 wherein the labeled oligonucleotide probes are labeled with a non-radioactive label.

42. The method of claim 37 wherein the labeled oligonucleotide probes are labeled with a fluorescent tag and the visualization step is accomplished by detecting the presence of fluorescence-tagged probes using a florescence-detecting scanner.

43. The method of claim 40 wherein the radioactive label is $^{32}P$.

44. The method of claim 41 wherein the non-radioactive label is peroxidase, biotin or digoxigenin.

45. A method of detecting the presence of an expanded trinucleotide repeat sequence of undetermined length in genomic DNA, wherein the expanded nucleotide repeat in the genomic DNA acts as a template for the annealing and ligation of repeat-specific oligonucleotides, comprising the steps of:

a) denaturing the genomic DNA to obtain single-stranded DNA;

b) annealing immediately ligatable trinucleotide repeat-specific oligonucleotides to the single-stranded DNA, said repeat-specific oligonucleotides consisting of a sequence being complementary to either strand of the expanded trinucleotide repeat to be detected, said repeat-specific oligonucleotides having unmodified ends and therefore capable of direct ligation;

c) ligating two or more repeat-specific oligonucleotides annealed in adjacent positions with a thermostable ligase to form multimer of the annealed repeat-specific oligonucleotides;

d) subjecting the annealed multimer to denaturing conditions to form single-stranded multimer of repeat-specific oligonucleotides; and e) repeating steps b) through d) to obtain a sufficient number of single-stranded multimer for detection whereby the presence of single-stranded multimer is an indication of the presence of an expanded trinucleotide repeat in the genomic DNA.

* * * * *